(12) United States Patent
Sandig et al.

(10) Patent No.: US 8,815,540 B2
(45) Date of Patent: Aug. 26, 2014

(54) PRODUCTIVITY AUGMENTING PROTEIN FACTOR, NOVEL CELL LINES AND USES THEREOF

(75) Inventors: Volker Sandig, Berlin (DE); Ingo Jordan, Berlin (DE); Elisabeth Brundke, Metzingen (DE)

(73) Assignee: Probiogen AG, Berlin (DE)

( * ) Notice: Subject to any disclaimer, the term of this patent is extended or adjusted under 35 U.S.C. 154(b) by 946 days.

(21) Appl. No.: 12/117,475

(22) Filed: May 8, 2008

(65) Prior Publication Data

US 2012/0164727 A1 Jun. 28, 2012

Related U.S. Application Data

(63) Continuation of application No. PCT/EP2006/068234, filed on Nov. 8, 2006.

(60) Provisional application No. 60/750,156, filed on Dec. 14, 2005.

(30) Foreign Application Priority Data

Nov. 8, 2005 (EP) ..................... 05110453

(51) Int. Cl.
| | |
|---|---|
| C12N 5/16 | (2006.01) |
| C12N 7/00 | (2006.01) |
| C07K 14/705 | (2006.01) |
| C07K 14/005 | (2006.01) |

(52) U.S. Cl.
CPC ........ C12N 7/00 (2013.01); *C12N 2710/16652* (2013.01); *C07K 2319/715* (2013.01); C07K 14/70567 (2013.01); *C07K 2319/60* (2013.01); C07K 14/005 (2013.01); *C12N 2710/10322* (2013.01); *C07K 2319/09* (2013.01); *C12N 2710/16622* (2013.01); *C12N 2510/02* (2013.01); *C07K 2319/00* (2013.01)
USPC ........................... 435/69.1; 435/325; 435/349

(58) Field of Classification Search
None
See application file for complete search history.

(56) References Cited

U.S. PATENT DOCUMENTS

| | | | | |
|---|---|---|---|---|
| 5,989,805 A | * | 11/1999 | Reilly et al. ....................... | 435/5 |
| 7,959,931 B2 | * | 6/2011 | Colegate et al. ............ | 424/209.1 |
| 2003/0108521 A1 | * | 6/2003 | Calatrava ..................... | 424/93.2 |

FOREIGN PATENT DOCUMENTS

| | | |
|---|---|---|
| WO | WO/99/57296 | 11/1999 |
| WO | 2005/042728 | 5/2005 |
| WO | WO/2005/042728 | 5/2005 |

OTHER PUBLICATIONS

Dhurandhar et al, Int. J. Obesity 25:990-996, 2001.*
Lieber et al, J. Virol. 73(11):9314-9324, 1999.*
Shayakhmetov et al, J. Virol. 76(3):1135-1143.*
Alexopoulou L, Holt AC, Medzhitov R, Flavell RA. "Recognition of double-stranded RNA and activation of NF-kappaB by Toll-like receptor 3." *Nature* 413:732-8 (Oct. 2001).
Caravokyri C, Leppard KN. "Constitutive episomal expression of polypeptide IX (pIX) in a 293-based cell line complements the deficiency of pIX mutant adenovirus type 5." *J Virol.* 69(11):6627-33 (Nov. 1995).
Colby WW, Shenk T. "Adenovirus type 5 virions can be assembled in vivo in the absence of detectable polypeptide IX." *J Virol.* 39(3):977-80 (Sep. 1981).
Fessler SP, Young CS. "Control of adenovirus early gene expression during the late phase of infection." *J Virol.* 72(5):4049-56 (May 1998).
Gao GP, Engdahl RK, Wilson JM. "A cell line for high-yield production of E1-deleted adenovirus vectors without the emergence of replication-competent virus." *Hum Gene Ther.* 11(1):213-9 (Jan. 2000).
Ghosh-Choudhury G, Haj-Ahmad Y, Graham FL. "Protein IX, a minor component of the human adenovirus capsid, is essential for the packaging of full length genomes." *EMBO J.* (6):1733-9 (Jun. 1987).
Graham FL, Smiley J, Russell WC, Nairn R. "Characteristics of a human cell line transformed by DNA from human adenovirus type 5." *J Gen Virol.* 36(1):59-74 (Jul. 1977).
Imler JL, Chartier C, Dreyer D, Dieterle A, Sainte-Marie M, Faure T, Pavirani A, Mehtali M. "Novel complementation cell lines derived from human lung carcinoma A549 cells support the growth of E1-deleted adenovirus vectors." *Gene Ther.* 3(1):75-84 (Jan. 1996).
Krougliak V, Graham FL. "Development of cell lines capable of complementing E1, E4, and protein IX defective adenovirus type 5 mutants." *Hum Gene Ther.* 6(12):1575-86 (Dec. 1995).
Ia Cour T, Kiemer L, Mølgaard A, Gupta R, Skriver K, Brunak S. "Analysis and prediction of leucine-rich nuclear export signals." *Protein Eng Des Sel.* 17(6):527-36 (Jun. 2004).
Leppard KN, Everett RD. "The adenovirus type 5 E1b 55K and E4 Orf3 proteins associate in infected cells and affect ND10 components." *J Gen Virol.* 80 ( Pt 4):997-1008 (Apr. 1999).
Louis N, Evelegh C, Graham FL. "Cloning and sequencing of the cellular-viral junctions from the human adenovirus type 5 transformed 293 cell line." *Virology* 233(2):423-9 (Jul. 7, 1997).
Möller A, Schmitz ML. "Viruses as hijackers of PML nuclear bodies." *Arch Immunol Ther Exp* (Warsz). 51(5):295-300 (2003).
Ojkic D, Nagy E. "The complete nucleotide sequence of fowl adenovirus type 8." *J Gen Virol.* 81(Pt 7):1833-7 (Jul. 2000).
Parks RJ. "Adenovirus protein IX: a new look at an old protein." *Mol Ther.* 11(1):19-25 (Jan. 2005).
Puvion-Dutilleul F, Chelbi-Alix MK, Koken M, Quignon F, Puvion E, de Thé H. "Adenovirus infection induces rearrangements in the intranuclear distribution of the nuclear body-associated PML protein." *Exp Cell Res.* 218(1):9-16 (May 1995).
Quignon F, De Bels F, Koken M, Feunteun J, Ameisen JC, de Thé H. "PML induces a novel caspase-independent death process." *Nat Genet.* 20(3):259-65 (Nov. 1998).

(Continued)

*Primary Examiner* — Kevin Hill
(74) *Attorney, Agent, or Firm* — McDonnell Boehnen Hulbert & Berghoff LLP

(57) ABSTRACT

The present invention provides a method for preparing a non-adenoviral target virus or target proteins utilizing a potent expression cell line having stably integrated into its genome a gene encoding a specific heterologous regulator protein.

5 Claims, 18 Drawing Sheets

(56) References Cited

OTHER PUBLICATIONS

Figure 1:
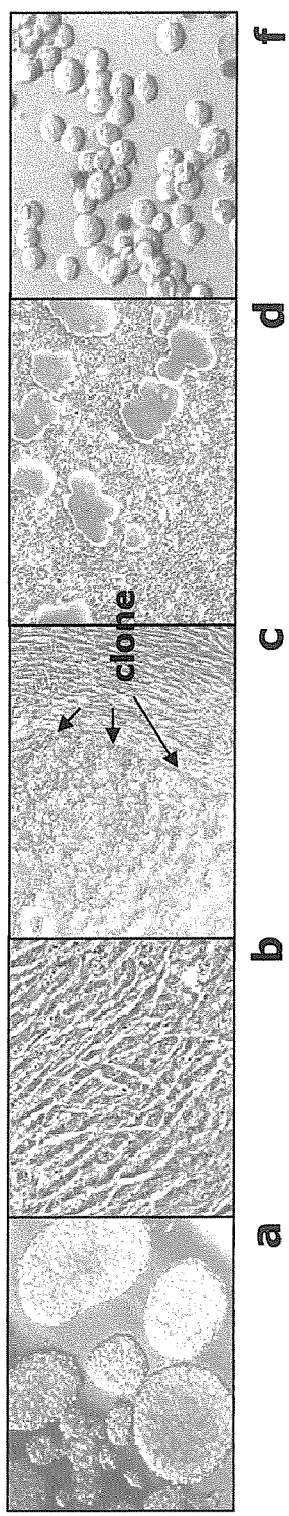

Spector DJ, Halbert DN, Raskas HJ. "Regulation of integrated adenovirus sequences during adenovirus infection of transformed cells." *J Virol*. 36(3):860-71 (Dec. 1980).

Wang ZG, Delva L, Gaboli M, Rivi R, Giorgio M, Cordon-Cardo C, Grosveld F, Pandolfi PP. "Role of PML in cell growth and the retinoic acid pathway." *Science* 279(5356):1547-51 (Mar. 6, 1998).

Uchida, et al. "Direct isolation of human central nervous system stem cells," (2000) PNAS, 97(26): 14720-14725.

\* cited by examiner

PRODUCTIVITY AUGMENTING PROTEIN FACTOR, NOVEL CELL LINES AND USES THEREOF

This application is a continuation of International Application Serial No. PCT/EP2006/068234, filed Nov. 8, 2006. This application claims benefit of European Application No. 05110453.7, filed Nov. 8, 2005 and U.S. Provisional Application No. 60/750,156, filed Dec. 14, 2005.

The present invention provides a method for preparing a non-adenoviral target virus or target proteins utilizing a potent expression cell line having stably integrated into its genome a gene encoding a specific heterologous regulator protein.

BACKGROUND OF THE INVENTION

Biopharmaceutical products from eukaryotic cells are an integral part of modern medicine. However, increased productivity and increased safety are important parameters that still require substantial optimization. The most crucial bottleneck in the efforts towards optimization is the cellular substrate itself. A safe transgene that can be introduced into cell lines already released for use in biopharmaceutical processes to increase product yields from the such manipulated cells is extremely valuable.

Adenoviruses are unenveloped (naked) double-stranded DNA viruses that infect a broad spectrum of animals. Among the best characterized members is the human adenovirus serotype 5 (Ad5). This virus is a frequent cause of common cold symptoms and infection often occurs in childhood.

Adenoviruses are amenable to genetic manipulation and replication incompetent adenoviruses, including Ad5 (GenBank accession number for sequence: AC_000008), are used as vectors in gene therapy and for therapeutic vaccination. To obtain replication incompetent viruses large regions of the genomic DNA are substituted with non-viral sequences. The missing viral functions are provided in trans by host cell lines that have been stably transfected with genes that are deleted in the vector. One of the earlier systems that were developed consist of adenoviral vectors deleted in the regulatory E1 region produced on cell lines providing the corresponding E1 proteins.

The most common cell line for this purpose is the 293 cell line. This line was generated in 1977 by transfection of fragmented adenoviral genomic DNA into primary human cells (Graham et al., J. Gen. Virol. 36, 59-74 (1977)), well before it was recognized that adenoviruses may serve as gene therapy vectors. The resulting cell line was subsequently shown to contain nucleotides 1 to 4344 of the genomic DNA (Louis et al., Virology 233, 423-429 (1997)) which includes the E1 region; this characterization demonstrated that the E1 region can be used to immortalize and transform primary cells.

Adjacent to the E1 region follows the gene for pIX ("protein 9"; nucleotides 3609 to 4031 on the genomic DNA). The promoter for pIX is embedded within the E1B component of the E1 region. A mechanism called promoter occlusion allows expression of pIX at a delayed-early time in the viral infection cycle at the onset of viral DNA replication with increasing copy number of viral DNA (Fessler and Young, J. Virol. 72, 4049-4056 (1998)). Although the gene is present within the 4344 nucleotides integrated into 293 cells, pIX expression cannot be detected even with sensitive radioactive labeling methods (Spector et al., J. Virol. 36, 860-871 (1980)).

As described above, replication deficient adenoviral vectors have been generated by deletion of the E1 region from the viral genome. E1 products are essential for viral replication and the function of the E1 region therefore had to be provided in trans via stable E1 transgenes in the adenovirus packaging cell (such as the 293 cell line). Because of the proximity to the E1 region the pIX gene caused frequent recombination between deleted adenoviral vectors and E1 in the host genome. This recombination event generated replication competent adenovirus (RCA), a serious contamination in vector preparations. To suppress this recombination event pIX was deleted from the adenovirus genome. In the course of these experiments it was recognized that pIX stabilizes the adenoviral capsid against thermal and steric stress by increasing the interaction of the main building blocks, the hexons (Colby and Shenk, J. Virol. 39, 977-980 (1981); Ghosh-Choudhury et al., EMBO J. 6, 1733-1739 (1987)). Morphogenesis in the absence of pIX yields temperature-sensitive viruses that cannot deliver genomic DNA molecules larger than 105% of the wild type 35938 base pairs. To still allow a normal packaging capacity and thermal stability the pIX protein was stably introduced into cell lines intended as packaging cells for adenovirus vectors (Krougliak and Graham, Hum. Gene Ther. 6, 1575-1586 (1995); WO 99/57296 and Imler et al., Gene Therapy 3, 75-84 (1996)).

Also with recognition that pIX decorates the surface of virions pIX-fusion proteins have been generated with the purpose to expand the host range of adenovirus vectors or to follow morphogenesis and the intracellular migration of virus particles (reviewed by Parks, Mol. Ther. 11, 19-25 (2005)).

Although clearly a structural protein, pIX also is implicated as regulatory protein for adenovirus replication. PIX is assumed to function as transactivator of transcription to augment E1A expression, a function possibly even excerted as a virokine by incoming PIX protein from the capsid at the infection step (reviewed by Parks, Mol. Ther. 11, 19-25 (2005)). PIX, together with early protein E4 Orf3, also is described to interact with sub-nuclear inclusions called PML bodies (Puvion-Dutilleul et al., Exp. Cell. Res. 218, 9-16 (1995); Leppard and Everett, J. Gen. Virol. 80, 997-1008 (1999)). These are dynamic aggregates of 250 nm to 500 nm in size and proposed to be involved in regulation of cell differentiation (Wang et al., Science 279, 1547-1551 (1998)), control of apoptosis (Quignon et al., Nature Gen. 20, 259-265 (1998)), and response to viral infection (Möller and Schmitz, Arch Immunol Ther Exp (Warsz) 51, 295-300 (2003)).

Because of its pleotropic effects we introduced the PIX protein into cell lines to examine whether PIX augments cell proliferation or production properties for biopharmaceutical products that are not related to adenovirus or adenoviral vectors. There is a general need for factors that modulate these properties in established cell lines.

For example, attenuated (weakened) viruses are promising vaccine candidates: upon inoculation they mimic a natural infection but allow more time for establishment of the desired protective immune response by the vaccinee. With increasing numbers of immunocompromised patients (for example, due to HIV infection) highly attenuated strains are desirable. Whereas attenuated strains still proceed towards (usually benign) infection highly attenuated strains are blocked at a cellular level even in absence of a functional immune system. A frequently used method to establish and maintain attenuation is to passage viruses on different host tissue. For example, measles and mumps viruses intended for human vaccination are passaged in primary cells, either in embryonated chicken eggs or cultures derived thereof. A new generation of vaccines is based on highly attenuated pox viruses that also depend on primary chicken cells for production. A cell line that can substitute for primary chicken cells and at the same time that even less efficiently protects itself against viral infection due to secondary manipulations such as introduction of the PIX transgene therefore provides a highly desirable substrate.

For other purposes a mammalian (rather than avian) cell line may be preferred. Such preferred cell lines already exist and have passed the examination by health authorities with respect to safety and risks posed by derived biopharmaceutical products. Here too, a secondary manipulation (such as introduction of the PIX transgene) to increase the spectrum of available applications or production efficiencies without compromising safety features is highly desirable.

SUMMARY OF THE INVENTION

Figure 2:
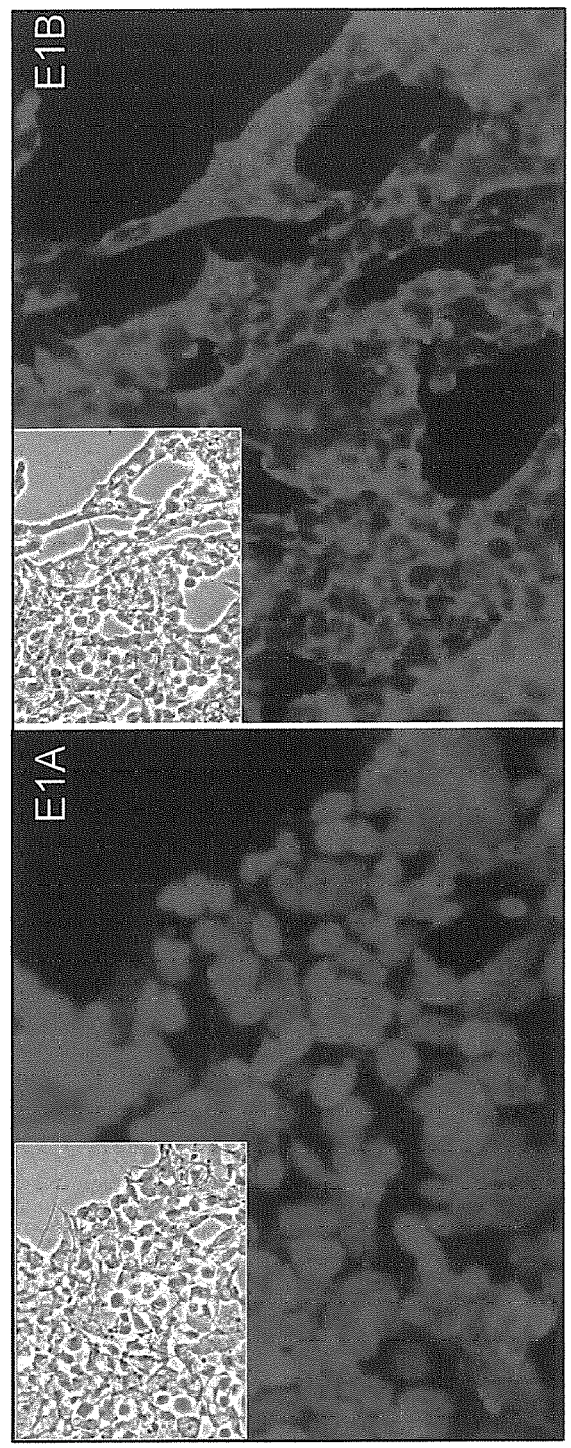

When preparing cell lines that have been stably transfected with adenoviral gene pIX (or a chimaeric fusion analogue thereof), we unexpectedly observed that pIX excerts a phenotypical effect in avian and human cells. For avian cells this is especially surprising because avian cells cannot be infected by human adenoviruses and aviadenoviruses (such as CELO or fowl adenovirus type 8) do not encode a PIX homologue (Ojkic and Nagy, J. Gen. Virol. 81, 1833-1837 (2000)). Furthermore, we observed that stable presence of PIX increases susceptibility of the cell to induction by double stranded RNA analogue, probably via toll like receptor 3. Probably in this context, we also unexpectedly observed that the presence of PIX protein increases yields of highly attenuated poxvirus in avian host cells. As poxvirus infected cells suffered less from induction by double stranded RNA analogue we may have found an interaction between PIX protein and anti-interferon genes of poxvirus that has not been described previously. We also observed a surprising increase in the yield of proteinaceous product (not only virus) released by a stably transfected cell line.

Thus, the present invention provides (1) a method for preparing a non-adenoviral target virus or one or more target proteins, which method comprises (a) culturing an expression cell being obtainable by infecting or transfecting a host cell, having stably integrated into its genome a gene coding for a Adenovirus PIX or a functional variant thereof as a heterologous regulator protein and stably expressing said regulator protein or the functional variant thereof, with said target virus, or with a vector carrying nucleic acid sequences encoding said target virus, or with a vector carrying nucleic acid sequences encoding said one or more target proteins (wherein the non-adenoviral target virus does not contain said regulator protein and the target protein(s) differs from said regulator protein or the functional variant thereof), and (b) isolating the target virus or the target protein(s);

(2) a preferred embodiment of (1) above, wherein said PIX protein or the functional variant thereof cooperates with non-cognate viral factors, modulates subcellular distribution of factors other than said protein, modulates transcription and/or cell growth, and enhances the productivity of the cell in the production of a virus not containing said regulator protein and in the production of a protein differing from said regulator protein or the functional variant thereof;

(3) a preferred embodiment of (1) and (2) above, where the adenovirus pIX is provided as a fusion protein with another protein that modulates or expands the activity or the subcellular distribution of the adenovirus pIX, for example is fused to retinoic acid receptor alpha, preferably is a fusion protein having the sequence shown in SEQ ID NO:4, or is fused to a GFP and contains an NLS, preferably is a fusion protein having the sequence shown in SEQ ID NO:23;

(4) a preferred embodiment of (1) to (3) above, wherein the host and expression cell is a vertebrate cell including mammalian cells and avian cells, preferably the mammalian cell is a human brain derived cell, and the avian cell is a duck retina derived cell or a duck somite derived cell;

(5) a preferred embodiment of (1) to (4) above, wherein the host and expression cell is derived from a human brain, preferably from human foetal brain, and most preferably is a NC5T11 cell, and said cell carries a nucleic acid sequence encoding Adenovirus PIX or a functional variant thereof as a heterologous regulator protein preferably said heterologous regulator protein is encoded by a nucleic acid shown in SEQ ID NO:1, SEQ ID NO:3 or SEQ ID NO: 22;

(6) a preferred embodiment of (5) above, wherein the host cell is a NC5T11#34 cell and the expression cell is derived from the NC5T11#34 cell, said NC5T11#34 cell being deposited with the DSMZ under Accession Number DSM ACC2744;

(7) a preferred embodiment of (1) to (4) above, wherein the host and expression cell is an avian cell, preferably is derived from duck retina or duck somite, and said cell carries a nucleic acid sequence encoding Adenovirus PIX or a functional variant thereof as a heterologous regulator protein, preferably said heterologous regulator protein is encoded by a nucleic acid shown in SEQ ID NO:1, SEQ ID NO:3 or SEQ ID NO: 22;

(8) a preferred embodiment of (7) above, wherein the host cell is a CR.PIX (17a11b) cell and the expression cell is derived from the CR.PIX (17a11b) cell, said CR.PIX (17a11b) cell being deposited with the DSMZ under accession number DSM ACC2749;

(9) an expression cell for producing a target virus or one or more target proteins as defined in (1) to (8) above, preferably the expression is as defined in (5) to (8) above;

(10) a method for preparing the expression cell as defined in (9) above, which comprises infecting or transfecting a host cell line as defined in (1) to (8) above with a virus, or with a vector carrying nucleic acid sequences encoding said virus or with a vector carrying nucleic acid sequences encoding said one or more target proteins;

(11) a host cell as defined in (5) to (8) above;

(12) a method for preparing the host cell of (11) above, which comprises transfecting an appropriate starting cell with a vector carrying said regulator protein or the functional variant thereof;

(13) the use of the expression cell as defined in (7) above for preparing a target virus or one or more target proteins;

(14) a fusion protein comprising at least one first domain comprising a regulator protein and at least one second domain comprising a protein or peptide acting as a transcription modulator and/or as a signal for subcellular targeting as defined in (2) or (3) above; and

(15) a nucleotide sequence encoding the fusion protein as defined in (14) above.

SHORT DESCRIPTION OF THE FIGURES

FIG. 1: History of the cell line NC5T11. A neurospheres of primary cells grown under serumfree conditions. B monolayer of primary cells grown in DMEM/F12 with 5% FCS. C primary focus two weeks after transfection with p79. the arrows indicate the border between primary and immortal cells. D homogenous adherent culture of immortalised cells in DMEM/F12 with 5% FCS. E suspension culture of NC5T11 in shaker tubes in EXcell VPRO.

FIG. 2: Immunofluorescense detecting E1A and E1B in NC5T11. After fixation with methanol cells were treated with rat antibodies directed against E1A and E1B 55k respectively followed by texas red conjugated anti rat antibodies. As shown in FIG. 2 all cells in the sample show nuclear staining typical for E1A and cytoplasmic staining for E1B. After fixation with methanol cells were treated with rat antibodies directed against E1A and E1B 55k respectively followed by texas red conjugated anti rat antibodies. As shown here, all cells in the sample show nuclear staining typical for E1A and cytoplasmic staining for E1B.

Figure 3:
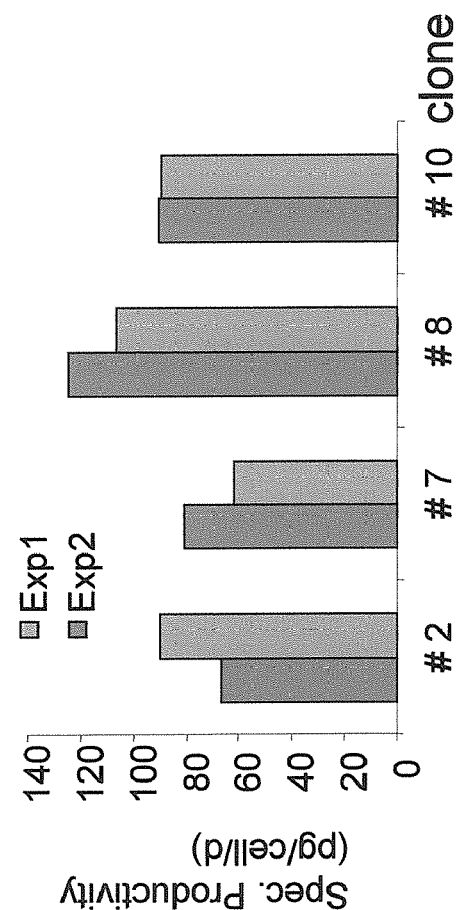

FIG. 3: Specific productivity of selected aat clones. Cell clones of NC5T11 transfected with C55 and selected with puromycin were seeded at $7 \times 10^4$ cells in 12 well plates, cell number and aat titer was determined on day 1, 2 and 3 after seeding and maximal cell specific productivity per day was calculated.

Figure 4:
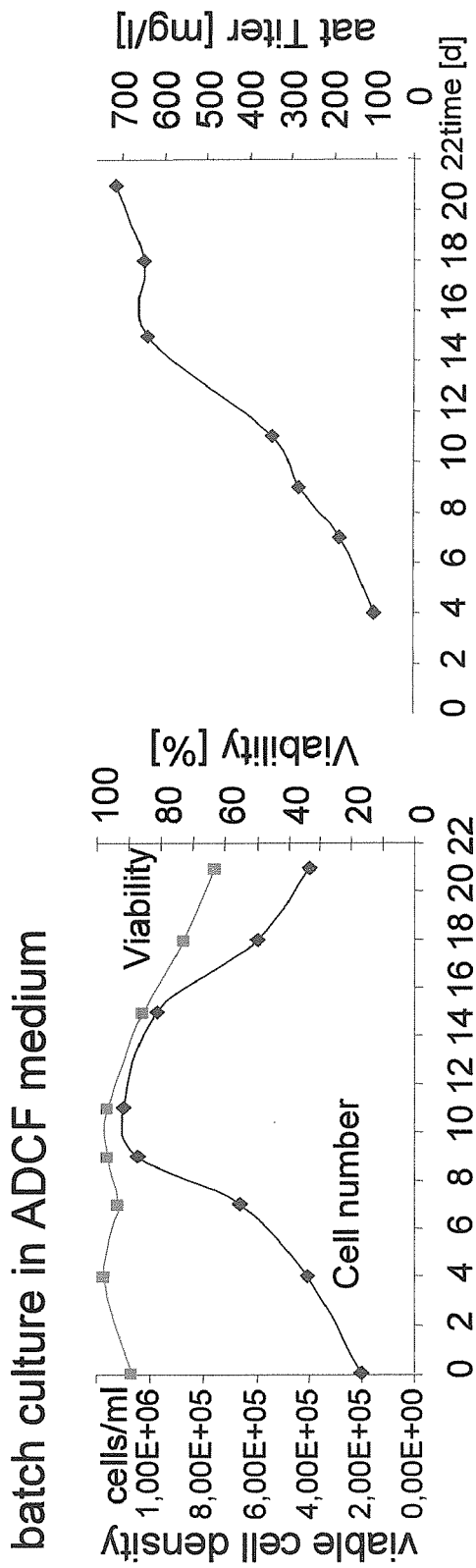

FIG. 4: Expression analysis of NC5T11puro#8 in shaker batch culture. Cells were seeded in 12 ml of EXCELL VPRO at $6 \times 10^4$ cells/ml in 50 ml polypropylene shaker tubes (TPP, Switzerland) with and subjected to rotation with a radius of 1 cm and a speed of 160 rpm. Samples of 200 µl were taken on days 4, 7, 9, 11, 15, 18 and 21. Cell density and viability was determined after staining with trypan blue using a haemocytometer.

Figure 5:
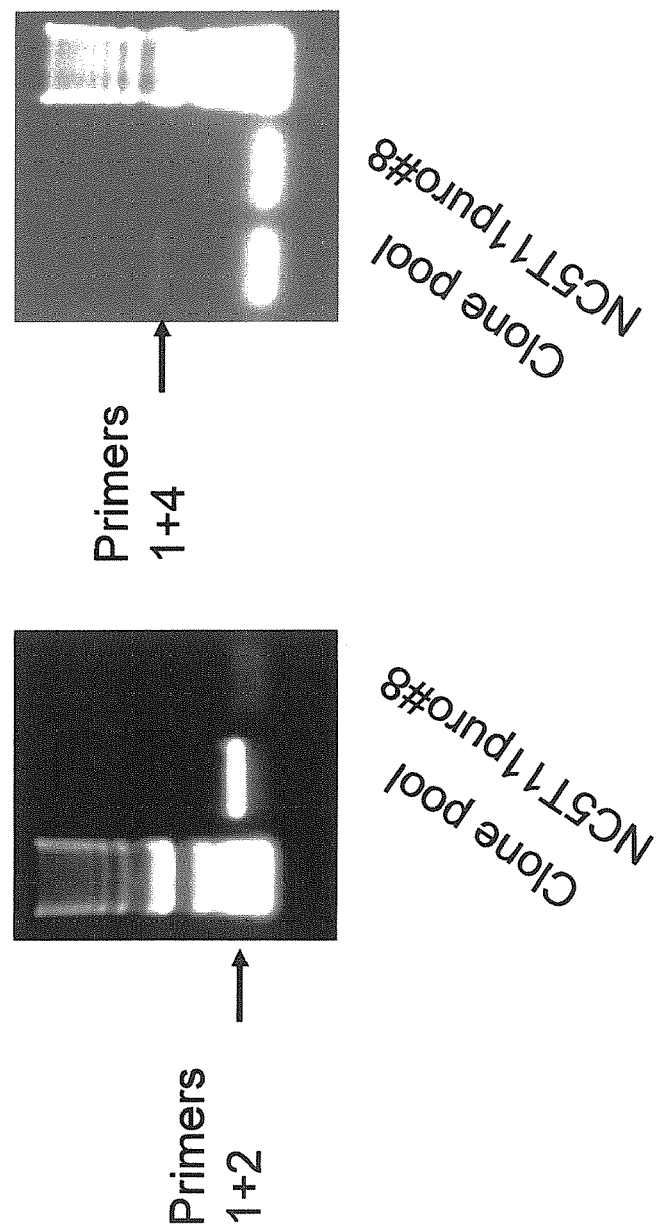

FIG. 5: Detection of the pIX-RARA cDNA by PCR in a clone pool. A clone pool carrying the pIXRARA gene was generated from NC5T11puro#8 by transfection with F67 and hygromycin selection. RNA was extracted using an RNA extraction kit (Machery Nagel, Germany) and cDNA was synthesized using AMV Reverse Transcriptase (Invitrogen). cDNAs for the pIX fragment alone or the whole pIXRARA gene were amplified with primer 1 and 1 and 164 respectively.

Figure 6:
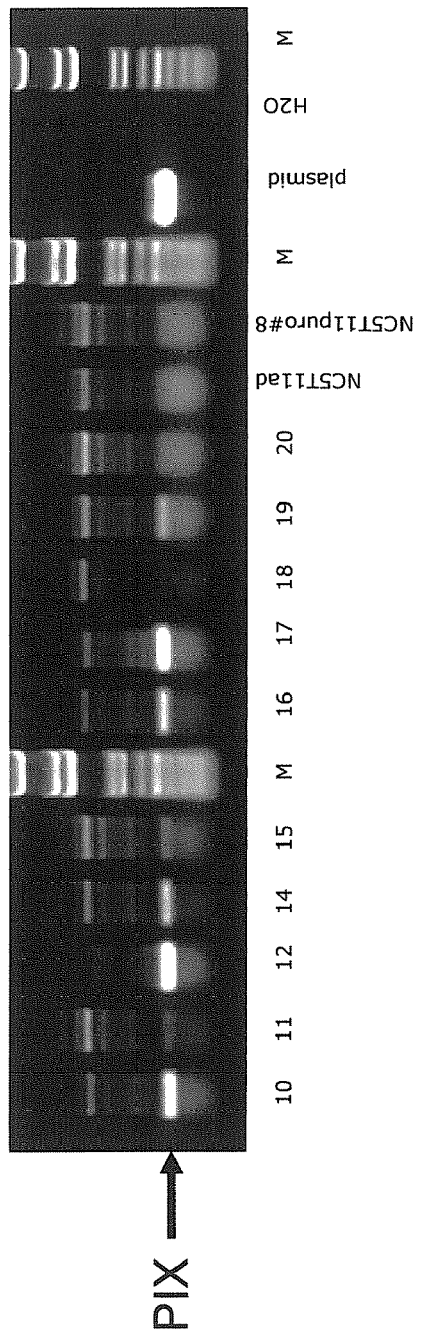

FIG. 6: Detection of the pIXs sequences as part of the fusion protein in hygromycin resistant subclones of NC5T11puro#8 and NC5T11(#34, 35, 36, 37, 38) by PCR. DNA was isolated from cell clones grown in 6 wells By lysis in SDS followed by phenol extraction and precipitation. DNA was amplified with Primers 1 and 2 for 28 cycles FIG. 7: Stability of the pIXRARA and pIX genes in stably transfected NC5T11 was determined relative to E1B: E1A+E1B and pIXRARA were introduced in separate transfections and E1 genes and have been maintained in the absence of selection for >2 years and are therefore considered stably integrated. Genomic DNA was isolated from selected cell clones at 2 time points: immediately after hyg selection stop (early); after 2 month in the absence of selection pressure (late). PIX and E1B DNA levels were determined by Real Time PCR.

Figure 8:
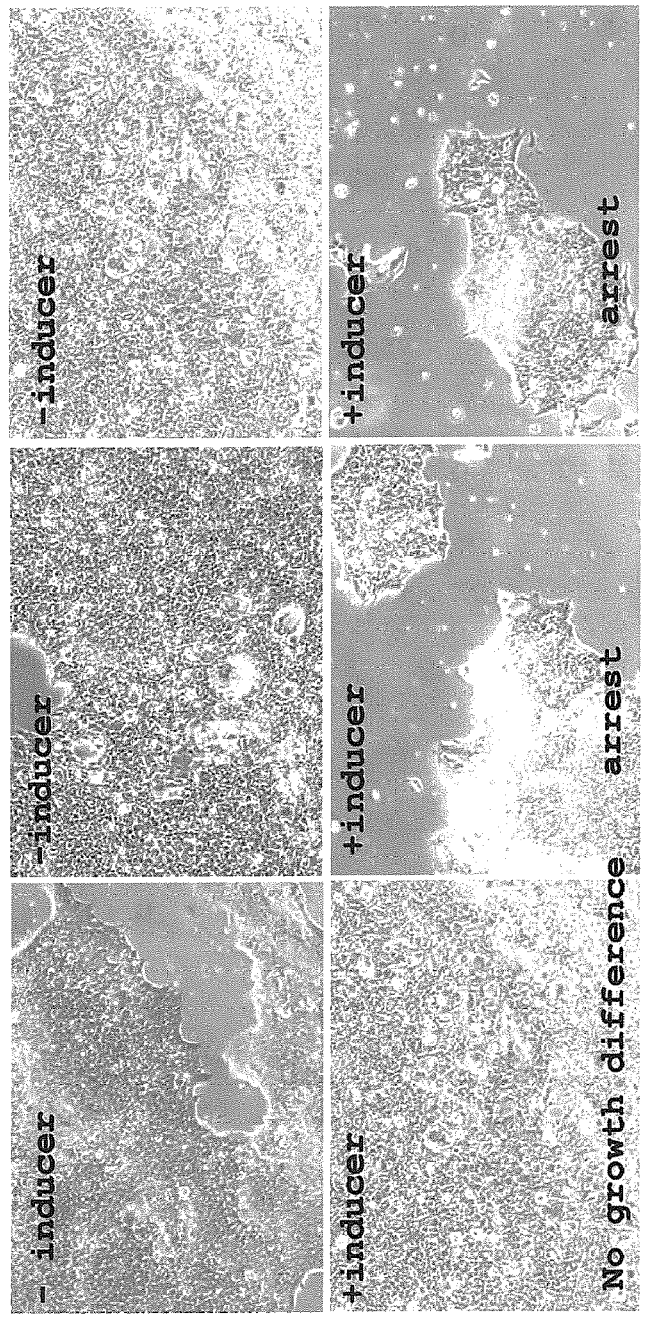

FIG. 8: Growth retardation induced by RA treatment in pIXRARA recombinant clones of NC5T11 and NC5T11puro#8. Cells were seeded at $2 \times 10^5$ in 6 well plates in the presence or absence of 6 µg/ml retinoic acid. Photos showing growth retardation in RA treated clones #12 and #34 but not in NC5T11 were taken 4 days after seeding using phase contrast imaging at a 4× magnification.

Figure 9:
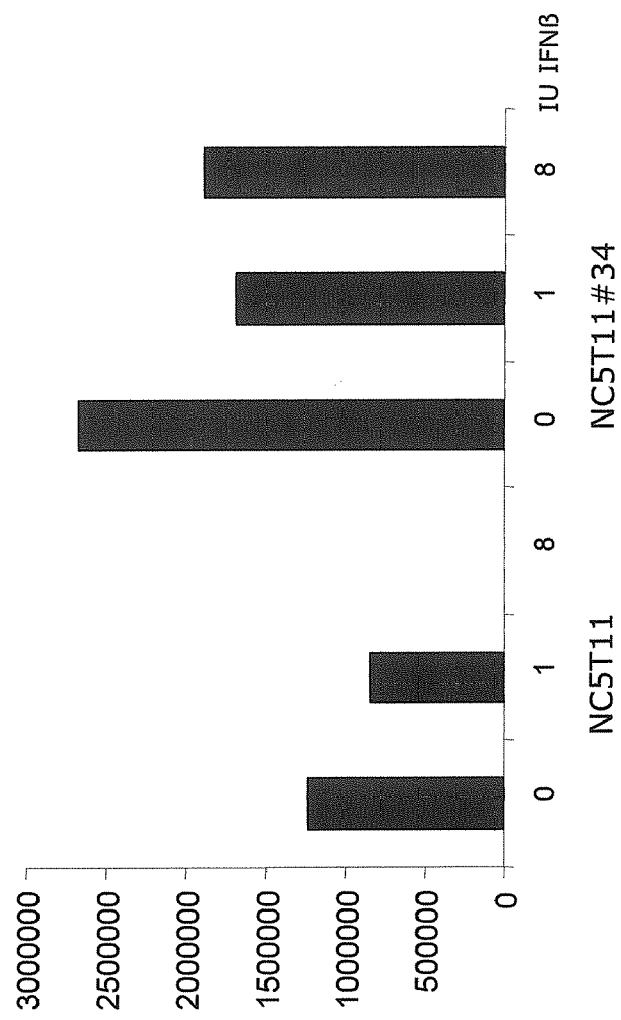

FIG. 9: PIXRARA prevents inhibition of virus replication by interferon. NC5T11 and NC5T11#34 cells were infected with EMCV an interferon sensitive virus at an MOI of 0.004 in cells treated with interferon beta. Cell lysates were subjected to titration by plaque formation on A549 cells.

Figure 10:
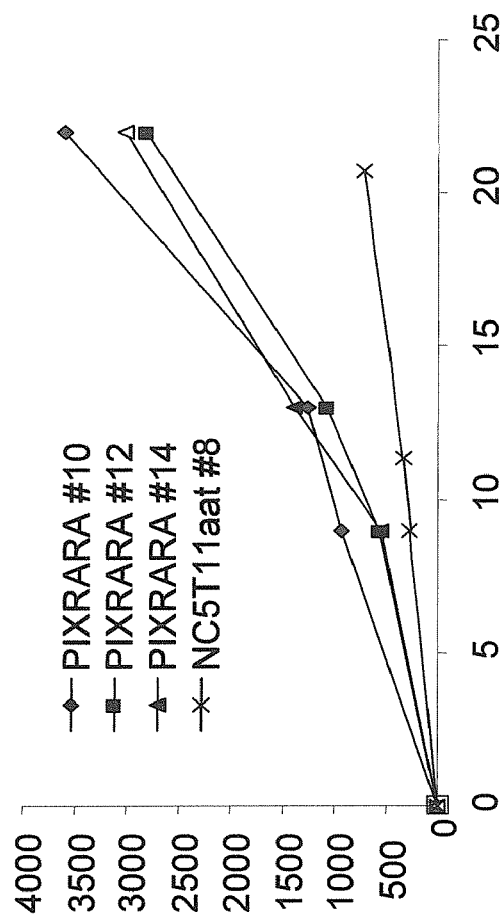

FIG. 10: Expression analysis of the cell line NC5T11puro#8 expressing alpha-1-antitrypsin from vector C55 and subclones #10, #12, #14 thereof, carrying the vector F67 (pEFpIX-RARA) in addition to C55. Cells were seeded in EXCELL VPRO (JRH Biosciences) at $6 \times 10^4$ cells/ml in 50 ml polypropylene shaker tubes (TPP, Switzerland) with a total volume of 12 ml and subjected to rotation with a radius of 1 cm and a speed of 160 rpm.

Figure 11:
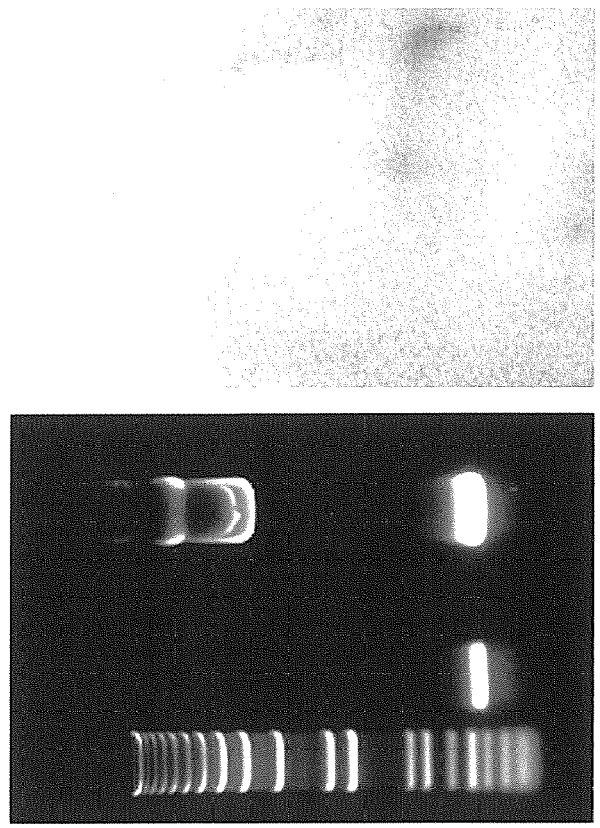

FIG. 11: Expression of PIX in duck retina CR cells. Left Panel: PCR reaction against PIX gene in genomic DNA of pIX cells. Gel loading from left to right: 1 kb-marker (Invitrogen); PCR on genomic DNA from CRpIX; non-template control; positive control with plasmid used in transfection of CRpIX. Right panel: Western blot for detection of pIX protein in CRpIX cells. Lane 1: 293 cells; lane 2: pIX protein in CRpIX cells.

Figure 12:
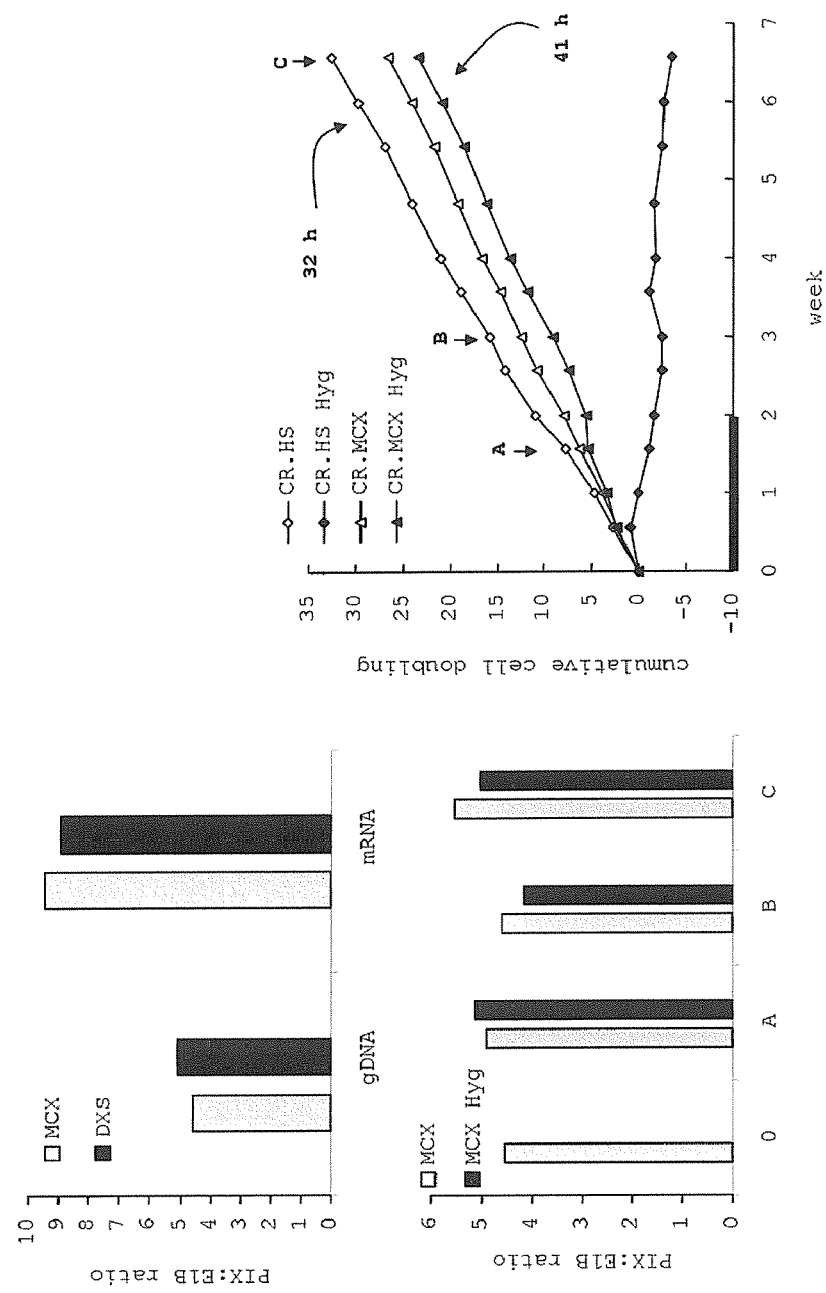

FIG. 12: Stable maintenance of PIX transgene in duck retina cells. Top-left panel: MCX and DXS are independent aliquots of a CRpIX clone cultivated for >3 months in parallel and without selection. After three months, TaqMan PCR was used to count the copy numbers of E1B and PIX transgene in MCX and DXS. As E1B transgene is maintained independent of PIX the ratio of the two genes is an indication of maintenance of PIX transgene. The ratio did not change between MCX and DXS. Furthermore, the ratio of PIX mRNA to E1B mRNA also did not change and PIX mRNA was in excess of E1B mRNA indicating expression of PIX. Right panel: MCX and parental (PIX-negative) CR.HS cells were cultivated with or without hygromycin selective pressure for 2 weeks (indicated by black bar on x-axis). At various time points genomic DNA was isolated (indicated by "A", "B", and "C") and subjected to TaqMan quantification (bottom-left). Whereas parental cells where killed by hygromycin MCX cells survived. The ratio of transgenes remained constant, again indicating stable maintenance of PIX transgene also in presence of selective pressure. Doubling time for parental cells is approx. 32 h but only 41 hours for MCX cells.

Figure 13:
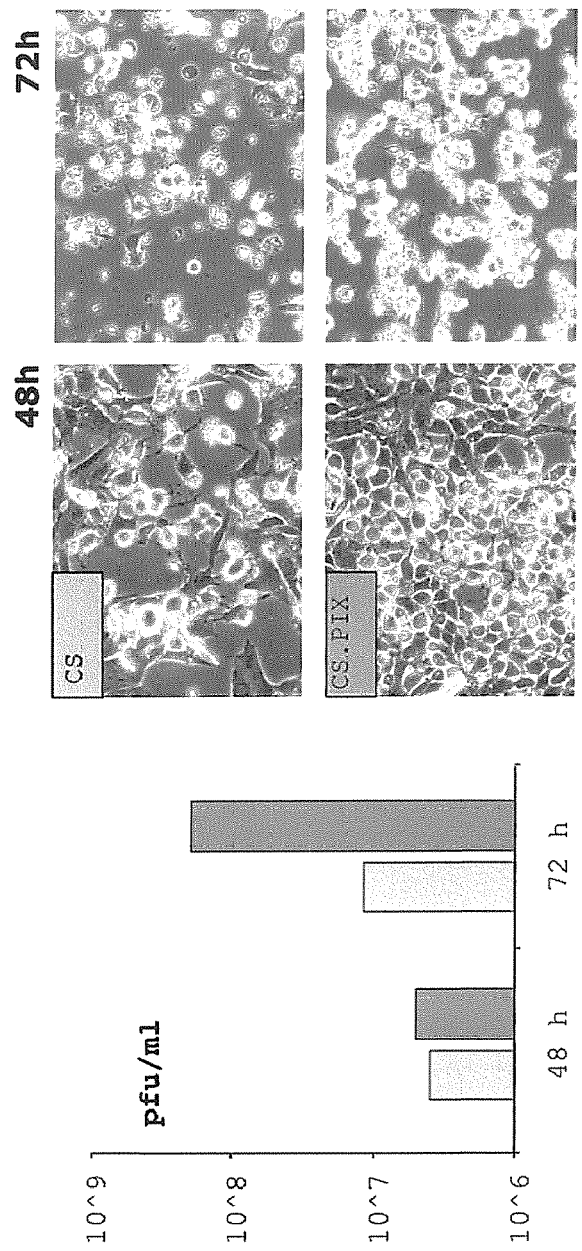

FIG. 13: PIX effect on Modified Vaccinia Ankara virus (MVA) replication in CS cells. CS and CSpIX cells were infected with MVA and assayed for MVA replication 48 h and 72 h post infection. The yield of MVA was significantly higher in PIX-positive CS cells. Also, as evident in the phase contrast microimage, cytopathic effect appeared delayed for CSpIX cells at 48 h. However, both cultures are susceptible to virus to similar degrees as complete lysis is evident at 72 h post infection.

Figure 14:
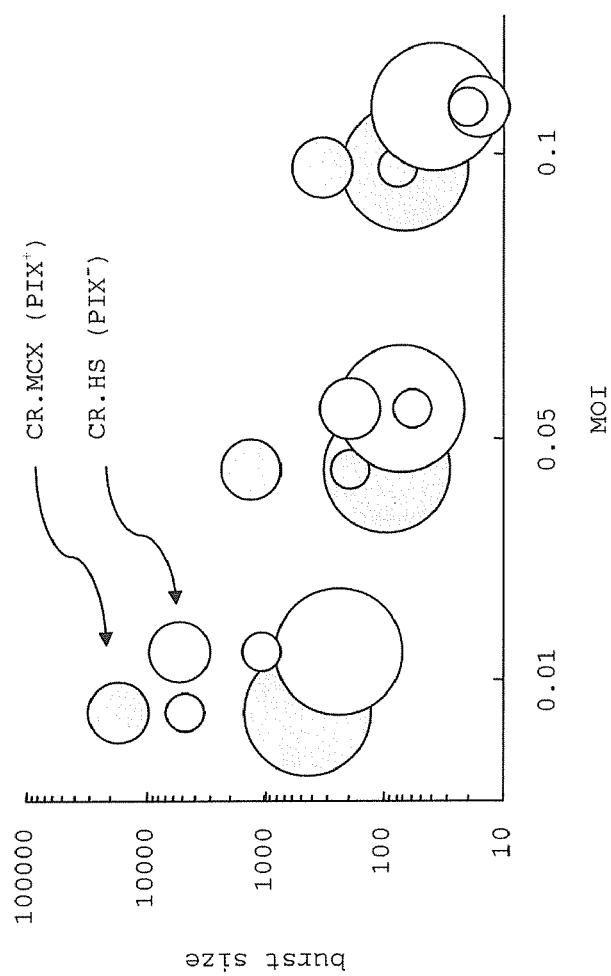

FIG. 14: PIX effect on MVA replication in CR cells. CR and CRpIX cells in suspension were infected with various multiplicities and at various seed cell densities. MVA yield was assayed 48 h post infection and is shown on the y-axis. The size of the bubbles displays seed cell densities. The filled bubbles show values for CRpIX cells, white bubbles show values for parental cells. In all configurations, PIX confers a clear increase in amplification rates of MVA.

Figure 15:
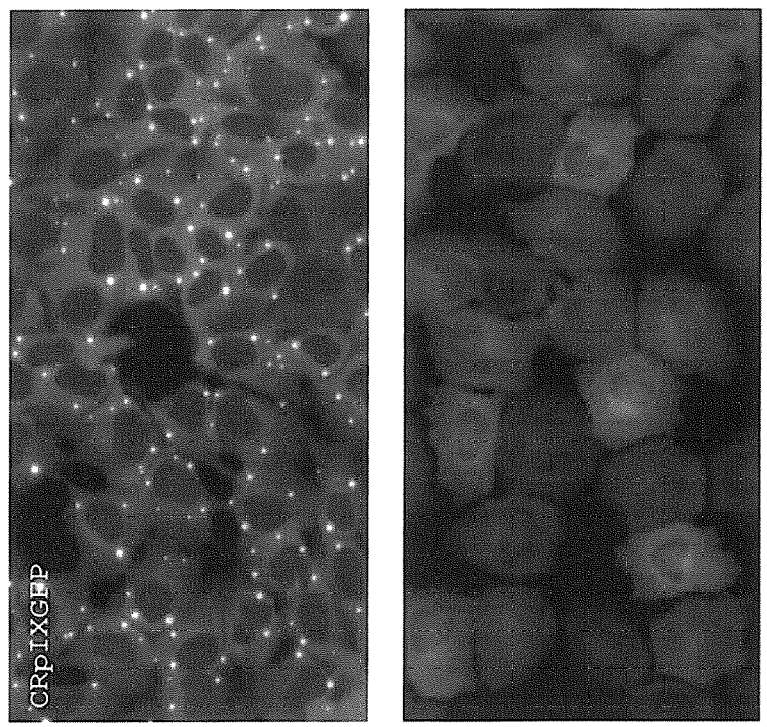

FIG. 15: Subcellular distribution of PIX-GFP in duck cells. GFP-tagged PIX appears in few cytoplasmic bright spots and diffuse cytoplasmatic staining largely excluding the nucleus. Other clones exhibit stronger, diffuse cytoplasmatic staining and more intense accumulation just outside the nucleus.

Figure 16:
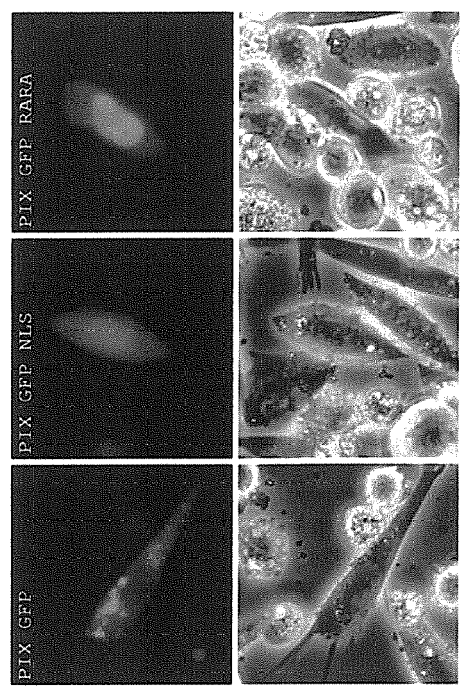

FIG. 16: Subcellular distribution of PIX-GFP variants in CHO cells. To investigate induced changes of PIX distribution within cells fusion variants were generated, including insertion of a nuclear localization site (NLS) and fusion to retinoic receptor alpha, a cellular protein that already contains an NLS. Shown are CHO cells transiently transfected with expression plasmids for PIX-GFP variants.

Figure 17:
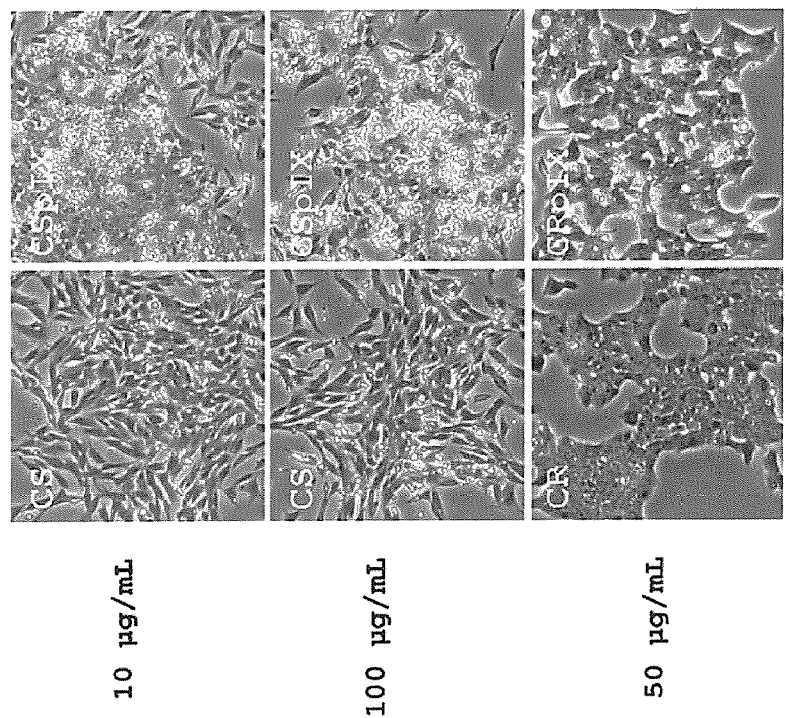

FIG. 17: Effect of interferon induction in presence of PIX. CSpIX and CRpIX cells were treated with poly I:poly C, a known inductor of type I interferon response and compared to parental cells. CSpIX cells reacted with greater sensitivity to poly I:poly C than CS cells. CRpIX and CR cells reacted comparably and to a lower extent than CS cells.

Figure 18:
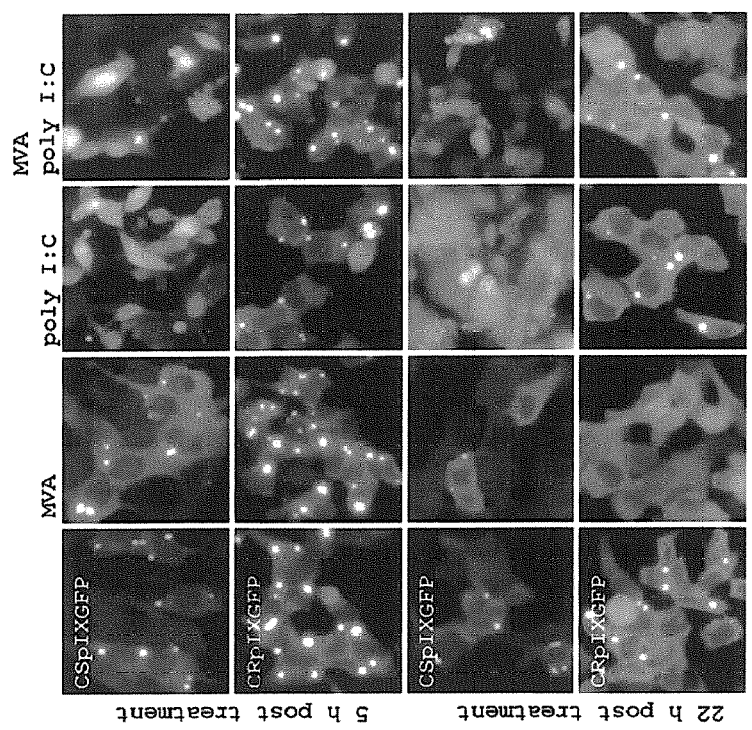

FIG. 18: Effect of MVA infection and interferon induction in presence of PIX-GFP. CSp9GFP and CRp9GFP cells were treated with poly I:poly C and infected with MVA at an M.O.I. of 0.1 as indicated. Again, CS-derived cells reacted more strongly to interferon induction. Surprisingly, bright PIX bodies appear to decrease in number upon induction or infection in both cell lines whereas overall signal intensity of PIX-GFP increases. Furthermore, the effect of poly I:poly C induction is ameliorated upon parallel infection with MVA as indicated by a greater number of CS cells still adherent 22 h after treatment.

DETAILED DESCRIPTION OF THE INVENTION

The method of embodiment (1) of the invention utilizes an expression cell having integrated into its genome a gene coding for a heterologous regulator protein, namely pIX or a functional variant thereof. Said regulator protein possesses the following properties:
1. It modulates transcription and, especially if linked to appropriate modulators or regulators, also influences cell growth.
2. It enhances productivity of the cell line with regard to the production of a virus not containing said regulator protein (i.e. the regulator protein is not a substitute for a protein deleted from the virus) and/or with regard to the production of a protein differing from said regulator protein or the functional variant thereof.

According to the invention the heterologous regulator protein is the adenovirus serotype 5 protein pIX (e.g. that having the aa sequence shown in SEQ ID NO:2), mutants (including addition, substitution, and/or deletion mutants) thereof, variants thereof (e.g. variants obtained from an adenovirus of a different serotype), and the like.

"Functional variant of the heterologous regulator protein" according to the invention include homologues from adenovirus other than serotyp 5, all types of mutation (addition, substitution and/or deletion) of particular amino acid residue(s) of the respective wild-type regulator protein, modification by fusion that further active protein or peptide sequences and the like. Particularly preferred are fusion proteins, namely fusion proteins comprising at least one first domain comprising a regulator protein as defined hereinbefore and at least one second domain comprising a protein or peptide acting as a transcription modulator. In a preferred embodiment of the invention said transcription modulator is a transcription factor including the retinoic acid receptor alpha, which may be present in complete or incomplete (i.e. truncated) form. The modulator may also be a transit peptide, which includes NLF sequences, e.g. that shown in SEQ ID NO:21. According to the invention the first and second domain(s) are either directly or via a peptide linker covalently attached to each other. Suitable peptide linkers include flexible and hydrophilic structures such as poly gly-ser.

The terms "cell" and "cell line" as used in the following detailed description refer to expression cells/expression cell lines and host cells/host cell lines.

According to the invention it is preferred that the heterologous regulator protein or the functional variant thereof is expressed in the cell in an amount of at least 1 pg/μg cellular protein, preferably at an amount of at least 10 pg/μg cellular protein so that its expression can be determined by Western-blotting.

In the cell of the invention the heterologous regulator protein or the functional variant thereof is preferably under control of a stabile homologous or heterologous promoter. Suitable promoters are constitutive cellular promoter or variants thereof such as the human translocation elongation factor 2 promoter. A particular variant of the human translocation elongation factor 2 promoter utilized within the invention has the sequence shown in SEQ ID NO:12. The sequence shown represents a "short" version of the promoter which is located on human chromosome 19:3,935,325-3,936,638 (human genome assembly May 2004) and provides for a stable medium level expression. For a stronger expression a "longer" version of the promoter located on chr19:3,935,349-3,938,957 (human genome assembly May 2004) may be used.

According to the invention the cell is a vertebrate cell including mammalian cells, avian cells and the like. Suitable mammalian cells are human cells, and rodent cells including mouse, rat, hamster, etc. Particularly preferred mammalian cells according to the invention are cells derived from human brain, particularly from human foetal brain, a mouse NSO or Sp2/0 cell, a BHk or CHO cell. Suitable avian cells are duck, chicken quail and goose cells. Particularly preferred avian cells according to the invention are cells derived from a duck retina-derived or somite-derived cell.

On the other hand, the cell of the invention may be derived from a primary cell or from a previously immortalized cell. Moreover, the cell may carry further immortalizing (viral) genes including an E1 protein of an adenovirus, such as the E1 protein of mastadenovirus group C type 5, and the like. Particularly preferred according to the present invention is that the cell further carries the adenovirus E1A and/or E1B gene shown in SEQ ID NO:5.

The cell utilized in the method of embodiment (1) of the invention may further carry functional sequences, e.g. sequences required for its application as expression cell such as selection marker sequences, splice donor/acceptor sites and/or recombinase recognition sequences allowing integration of a target nucleic acid sequence to be expressed in the cell, etc.

The "infecting", "transfecting" and "transforming" effected within the method of embodiments (1), (10) and (12) of the invention may be performed according to standard procedures known to the skilled person. Said methods may further encompass suitable selection, isolation and expansion steps, if required.

In the method of embodiment (1) the target virus includes from wild-type, mutated or deleted virus, cold adapted or attenuated virus, vaccine strains, viral vectors carrying heterologous gene(s), viral vectors such as lentivirus, poxvirus, adeno associated virus (aav), herpesvirus, flavivirus and the like.

Further, in the method of embodiment (1) the one or more target proteins include antibodies, recombinant proteins such as erythropoetin, alpha-1-antitrypsin, blood clotting factors VIII and IX and interferons, viral antigens such as influenza HA and NA, and M, HBV-S, herpes G protein and rabies G protein, peptide hormones and the like. Although the method allows the production of cells capable of contemporary expression of more than one target proteins, it is particularly preferred that it encodes only one target protein.

The culturing and isolation of the method of embodiment (1) of the invention may be performed according to standard procedures readily available to the skilled person. Said method may further include standard purification steps as well as subsequent modification steps of the target virus or target protein(s).

Concerning the preferred embodiments of the expression and host cell lines of embodiments (9) and (11), respectively, as well as the production methods for said cell lines of embodiments (10) and (12), it is referred to the detailed discussion provided hereinbefore in connection with embodiment (1).

According to embodiments (14) and (15) the invention provides for a fusion protein comprising at least one first domain comprising a regulator protein and at least one second domain comprising a protein or peptide acting as a transcription modulator as defined hereinbefore, and for a nucleotide sequence encoding said fusion protein, respectively. The invention also relates to the use of said fusion protein (e.g. in diagnostic and pharmaceutical applications, etc.) and of the nucleotide sequence encoding it of embodiments (14) and (15), respectively, e.g. in all types of vector constructs, cell lines, tissue culture, transgenic animals, etc.

The cell line NC5T11#34 was deposited with the DSMZ-Deutsche Sammlung von Mikroorganismen und Zellkulturen GmbH, Mascheroder Weg 1b, 38124 Braunschweig, Germany on Nov. 4, 2005 under accession number DSM ACC2744. The cell line CR.PIX (17a11b) was deposited with the DSMZ-Deutsche Sammlung von Mikroorganismen und Zellkulturen GmbH, Mascheroder Weg 1b, 38124 Braunschweig, Germany on Nov. 24, 2005 under accession number DSM ACC2749.

The invention will be explained in more detail by means of the following examples, which are, however, not to be construed to limit the invention.

EXAMPLES

Example 1

Development of the Cell Line NC5T11

The cell line was developed from a mixture of cells from foetal brain by immortali-sation with adenovirus 5 E1A and B genes by nonviral transfection.

A tissue sample was taken from the periventricular zone of the brain of a foetus after induced abortion. It was dissected with scissors and homogenised by aspiration with a tissue culture pipette in neuronal culture medium based on DEMEM/F12 containing 20 ng/ml hFGF (Invitrogen, Carlsbad, Calif. 92008, USA), 20 ng/ml hEGF (Invitrogen), 1×N2 supplement (Invitrogen) and 8 µg/ml heparin (Sigma Aldrich, St. Louis, USA). Cells were sedimented at 200 g for 3 min. Viability of cells was assessed using trypan blue and propidium jodide using a flow cytometer (BD Biosciences, Jose, Calif. 95131, USA). The viability was 75%. $0.5 \times 10^6$ cells were seeded into T25 flasks. Cells were incubated at 37° C. and 5% $CO_2$. The cells formed neurospheres by day 5 of the culture. Neurospheres are shown in FIG. 1A. On day 8 cells were transferred to DMEM/F12 supplemented with 5% FCS to allow for attachment and to stimulate proliferation. Cells formed a homogenous monolayer as shown in FIG. 1B and were passaged 1:5 once per week. This primary neural cell culture was named NC5.

After 2 weeks in serum containing medium cells were transfected with vector p79 in subconfluent 6-well plates using Effectene (Qiagen, 40724 Hilden, Germany) as a transfection reagent following the manufacturers instructions. The plasmid p79 contains the following elements: The pBluescript (Stratagene, USA) serves as plasmid backbone, in which the ampicillin resistance marker was replaced by the kanamycin resistance gene driven by a bacterial promoter which allows for growth and selection in E. coli. The vector harbours a fragment form wild type adenovirus type 5 (SEQ ID NO:5) containing the open reading frames for E1A (splice variants 13S and 12S with or without the CR3 domain respectively) and E1B 55k and 19k as well as sequences upstream of E1A. The E1A gene is preceded by the phosphoglycerate kinase promoter (mouse). The adenovirus sequences are followed by the polyadenylation signal from the Herpes simplex thymidine kinase gene, serving as a replacement for the E1B polyadenylation signal. Elements were obtained from the respective organisms or from donor plasmids by PCR and cloned using conventional recombinant DNA techniques and verified by sequencing. Two days after transfection cells were trypsinized and transferred to a 10 cm dish. Two weeks later foci of small cells with a high nucleus/Cytoplasma ratio and clearly distinguishable borders were formed (FIG. 1C) in transfected but not in mock treated cells. From the 11$^{th}$ transfection eight independent foci were isolated with and trypsin using cloning cylinders (Corning, USA), seeded to wells of a 24 well plate and expanded via 12 well plate, 6 well plate to T25 flasks. All isolated foci contained two types of cells: small cells with sharp borders and extended fibroblast like cells.

Three weeks posttransfection 15 additional clones became visible in transfection T11 some of which may originate from remaining cells of already isolated primary clones.

Clones T11a.1 and T11a.6 showed the fastest growth and were cryopreserved in DMEM/F12, 10% DMSO, 25% serum 8 weeks post transfection. At this time all clones still contained a fraction of cells with enlarged cytoplasma resembling primary phenotype. However, with a split ratio of 1:5 for T11a.1 and T11a.6 they were overgrown and eliminated approximately 3 month after transfection. Immunofluerescence experiments were carried out to associate the changed morphology with expression of E1A and E1B. After fixation with methanol cells were treated with rat antibodies directed against E1A and E1B 55k respectively followed by texas red conjugated anti rat antibodies. As shown in FIG. 2 all cells in the sample show nuclear staining typical for E1A and cytoplasmic staining for E1B.

Three month after transfection clone T11a.1 and T11a.6 were transferred to serum-free medium ProPER (Cambrex, Belgium) by seeding $1.6 \times 10^6$ cells after trypsin treatment. Cells were harvested by centrifugation and medium was exchanged by centrifugation once a week. The cell population survived but even six month after transfection cells still showed a low viability and grew with a high doubling time of 60-80 h.

When the cells were transferred back to DMEM/F12 with 5% FCS after 3 month in ProPER medium, a homogenous and highly viable culture with a doubling time of 40 h has formed for both clones. T11a.1 was chosen as the more most robust cell clone for further experiments and named NC5T11 (FIG. 1D)

Example 2

Establishment of NC5T11puro Clone#8

Protein production in a cell line depends on efficient transfection and selection methods. The suitability of commonly used selection markers G418, puromycin, hygromycin, blasticidin, MTX, histidinol for NC5T11 was unknown. In a first evaluation step different commercially available transfection reagents Lipofectamine (Invitrogene), Fugene (Roche, Germany), Polyfect (Qiagen) and Effectene were tested following the manufacturers protocols. The plasmid pEGFP-N1 (Clonetech, USA) expressing gfp from the human CMV promoter was used to determine transient transfection efficacy. The highest efficiency was obtained with Effectene (Qiagen)

reaching 20-50% depending on cell density when applied to adherent cells growing in DMEM/F12 10% FCS.

To test selection marker genes, expression vectors were constructed containing the human alpha-1-antitrypsin (aat) gene under control of the human CMV promoter followed by the bovine growth hormone PolyA signal and the respective selection marker controlled by a weak promoter. More specifically, to test for puromycin selection, vector C55 was used which contains the puromycin resistance gene driven by the human PGK promoter followed by the SV40 early polyadenylation signal.

After transfection cells were seeded in DMEM/F12 5% FCS containing 0.75 µg/ml puromycin and selected for 3 weeks with weekly medium exchange. A clone pool was generated and expression was verified by immunofluoroescense using a goat polyclonal anti-alpha-1-antitrypsin antibody (Innogenetics, USA) followed by a biotin labelled secondary rabbit anti-goat antibody and a streptavidin-Texas Red conjugate.

To isolate individual cell clones 10000 cells of the clone pool were seeded in a 15 cm dish. After 4 weeks clones were isolated using clone cylinders (Corning) and clones #1, 2, 7, 8, 9, 10 were analysed for aat expression. More specifically, cells were seeded at $7 \times 10^4$ cells in 12 well plates, cell number and aat expression was determined. Calculated cell specific productivity rates are given in FIG. 3. Clone NC5T11puro#8 shows a specific productivity above 100 pg/cell·day and was chosen for further development.

Example 3

Shift of NC5T11 and NC5T11puro#8 to Production Medium and Expression Analysis in Shaker Batch Culture The growth rate of both NC5T11 and NC5T11puro#8 in ProPER medium (Cambrex) was approximately two times reduced compared to serum containing medium. Therefore, Xcell VPRO (JRH Biosciences) was tested as an alternative. Adaptation was done by direct seeding of $4.5 \times 10^6$ cells in 5 ml EXCELL VPRO in a T25 flask. After 2 weeks cell growth reinitiated and a weekly split ratio of 1:3 was established. As a next step both clones were adapted to growth in the presence of shear stress. Cells were seeded in 12 ml of EXCELL VPRO at $6 \times 10^4$ cells/ml in 50 ml polypropylene shaker tubes (TPP, Switzerland) with and subjected to rotation with a radius of 1 cm and a speed of 160 rpm. After repeated passages batch assays were performed o determine maximal cell densities and product accumulation during exponential and stationary growth phases. The following observations were made: Clone NC511puro showed a high viability which was maintained above 70% until day 18. Maximal cell density did not exceed $1 \times 10^6$. Product accumulation continued during stationary phase (FIG. 5). It was concluded that specific media development or further cell improvement will be required to achieve a high cell density comparable to those obtained with CHO cells. This will likely result in a substantial increased product titers.

Example 4

Construction of the Fusion Protein pIX-RARA and Integration Vectors for Both pIX-RARA and pIX Sequences for adenovirus PIX and retinoic acid receptor alpha (RARA) were obtained by PCR from adenovirus type 5 and human genomic DNA respectively using primers

```
1. AACCAGCGCTACCATGAGCACCAACTCGT        (SEQ ID NO: 6)

2. AATGGTGGCAACCGCATTGGGAGGGGAGG        (SEQ ID NO: 7)
for PIX and

3. CCAATGCGGTTGCCACCATTGAGACCCAGA       (SEQ ID NO: 8)

4. AAGGAGCGCTGGCGAGGGCTGTGTCCAT         (SEQ ID NO: 9)
for RARA.
```

Both Fragments were amplified separately. An overlap between primers 2 and 3 allowed to connect both fragments via PCR using primers 3 and 4. The fusion gene was cloned into vector pEFpromhyg resulting in pEFpIXRARA. This vector contains the human elongation factor 2 promoter located on chr19:3,935,325-3,936,638 (human genome assembly May 2004; SEQ ID NO:12). It contains upstream elements and the first intron of the EF2gene. The natural start codon of EF2, located 5' to the first intron, was removed by mutagenesis. In the vector, pEFpromhyg, the EF2 sequence is followed by the unique restriction site (AfeI) used for insertion of pIX-RARA. An internal ribosome binding site following the AF1 site allows expression of the hygromycin resistance gene as a second open reading frame in a joined RNA with pIX-RARA. This configuration supports pIX-RARA expression in all hygromycin resistant cells.

The gene for wt pIX was amplified using primers AAC-CAGCGCTACCATGAGCACCA-ACTCGT (SEQ ID NO:10) and ACCGAGCGCTTGTTTTAAACCGCATTGG (SEQ ID NO:11) and integrated into the Afe site of pEFpromhyg instead of pIX-RARA to yield pEFpIX.

Example 5

Figure 7:
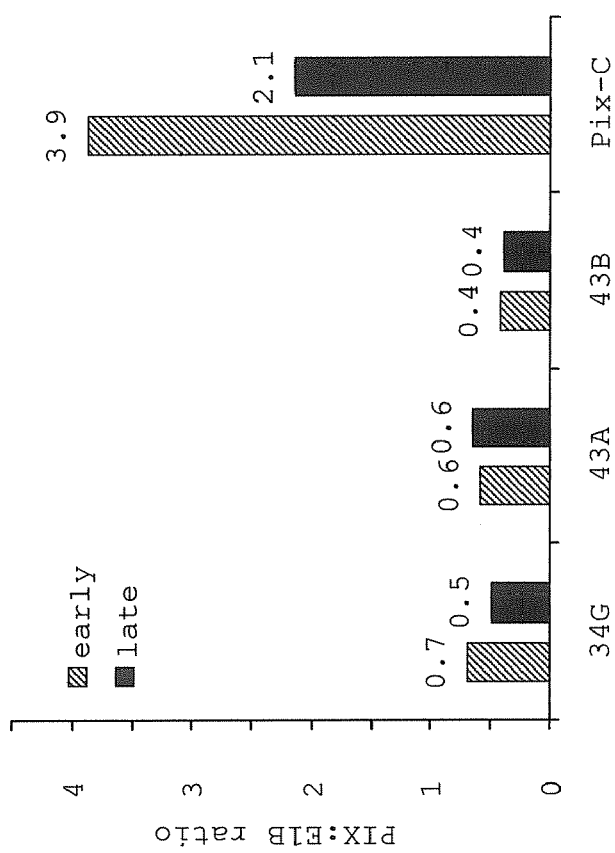

Modification of the Cell Lines NC5T11 and NC5T11puro#8 with the PIX Gene and the PIX-retinoic Acid Receptor Fusion Protein Cell clones NC5T11 and NC5T11puro#8 were prepared for transfection in 6-well plates by seeding $1.3 \times 10^6$ cells/well in DMEM/F12, 5% FCS. Plasmid F67 (pEFpIXRARA) and plasmid F76 (pEFpIX) were linearised with restriction enzyme Asp700 (Roche) and transfected after ethanol precipitation using Effectene (Qiagen): DNA was mixed with 16 µl Enhancer and 200 µl EC Buffer. After 2 min at room temperature, 18 µl Effectene were added and liposome formation allowed for 10 min at room temperature. The transfection mix was added to 1 ml culture volume on cells seeded to 80% confluency in 6-well plates on the previous day. High transfection efficiency was confirmed with a parallel transfection of pEGFP-N1 (Clontech, Palo Alto, Calif. 94303-4230, USA). One day after transfection medium was exchanged to DMEM/F12 with 10% FCS and 75 or 100 µg/ml (NC5T11) and 50 µg/ml µg/ml (NC5T11puro#8) hygromycin was added. Selection medium war replaced two times per week. After 18 days 15-20 clear clones became visible in each of the wells. Clone pools were treated with trypsin and selection was continued for two more weeks. Clone pools were tested for expression of PIXRARA by RTPCR. A strong signal was detected with primers 1 and 2, a weaker signal with primers 1 and 4 in most of the clone pools. To isolate individual cell clones 10000 and 1000 cells of the clone pool were seeded into 15 cm dishes. After 4 weeks clones were isolated using clone cylinders (Corning) For clones resulting from transfection of F76 a different strategy was applied. Clone pools were treated with trypsin, transferred to a 50 ml shaker tube in EXCELL VPRO containing 75 µg/ml hygromycin and after 2 weeks of suspension culture 2000 viable cells were mixed with 12 ml clone matrix (Genetix, UK), seeded into a six-well plate (Greiner)(2 ml/well) and subjected automated colony picking (clonepixFL, Genetics, UK). Clones originating from NC5T11puro#8 were given numbers #10-21. Clones originating from NC5T11 were given #34-45. Clones transfected with pEF2PIX were named NC5T11PIXA-NC5T11PIXE. Clones were tested for the presence of the respective vector by PCR. An initial test using primers 1 and 2 is provided in FIG. 6. All clones showing a positive signal were shifted to growth in ExCell VPRO. Readaptation was done by direct seeding of $4.5 \times 10^6$ cells in 5 ml EXCELL VPRO in a T25 flask. After 6 weeks in stationary culture cells were transferred to 50 ml polypropylene shaker tubes (TPP, Switzerland) at a seeding density of $6 \times 10^4$ cells/ml in EXCELL VPRO with a total volume of 12 ml and subjected to rotation with a radius of 1 cm and a speed of 160 rpm. Clones #10, #12, #14 (NC5T11puro#8pIXRARA) and #34, #43 (NC5T11pIXRARA) and NC5T11PIXB, NC5T11PIXC were chosen for there highest viability under shear stress. Clones #34, 43 and NC5T11PIXC were recloned and analysed for stability of the integrated DNA. Stability was assessed determining the gene ratio between PIX and E1B because E1A+E1B and pIXRARA were introduced in separate transfections and E1 genes were introduced and have been maintained in the absence of selection for >2 years and are therefore considered stably integrated. Genomic DNA was isolated from selected cell clones at 2 time points: immediately after hyg selection stop (early); after 2 month in the absence of selection pressure (late). PIX and E1B DNA levels were determined by Real Time PCR (ABI 7000, CYBR Green) at 2 DNA concentrations Examples of this evaluation are shown in FIG. 7 The vector pEF2PIXRARA is stably maintained in subclones of #34 and #43 with approximately 0.4-0.6 copies of PIXRARA per E1B. Clone NC5T11PIXC originally contains 4 copies of pIX per E1B. This number is reduced twofold during the cause of the experiment.

Example 6

Retinoic Acid Dependent Growth of NC5T11pIX-RARA

Retinoic acid (RA) is an inducer of cell differentiation. Differentiation is typically associated with reduced cell growth. The response to RA depends on expression of retinoic receptor alpha, a transcription factor activated by RA. RA has a profound effect on PML (promyelocytic leukaemia) reverting the transformed phenotype by growth arrest.

As shown in FIG. 8 RA treatment at a concentration of 6 µg/ml did not have any effect on growth of either NC5T11 or the alpha-1-antitrypsin expressing clone NC5T11puro#8. However, growth of clones #14 (NC5T11puro#8pIXRARA) and #34 (NC5T11pIXRARA) were arrested by treatment with 6 µg/ml for 5 days in adherent culture in DMEM/F12 with 5% FCS.

Example 7

PIXRARA Prevents Inhibition of Virus Replication by Interferon

NC5 T11 and NC5T11#34 cells were seeded into 6 well plates at $8.0 \times 10^5$ cells/well in DMEM/F12 5% FCS. After 12 h interferon beta (rebif 44 of Serono) was added to wells at a concentration of 1 and 8 IU/ml. After 30 min interferon treated cells and control cells of both NC5 T11 and NC5T11#34 were infected with Encephalomyocarditis virus (EMCV) at a multiplicity of infection (MOI) of 0.004. After 24 h, cultures were harvested and frozen at −80° C. to disrupt the cells. This suspension was thawed and cleared by centrifugation with 800×g for 10 min. Lysates were subjected to virus titeration by plaque assay on A549 cells: In brief, A549 cells were seeded to 24 well plates and grown to reach confluency, incubated for 30 minutes with cleared lysates diluted 10 to $2 \times 10^8$ fold, overlayed with 0.2% low gelling agarose type VII in RPMI 10% FCS and incubated at 37° C. for 24 h. The agarose layer was aspirated, cells were fixed with 2% glutaraldeyhde in PBS for 20 min at 20° C., washed with water and incubated for 30 min at room temperature with 1% Kristallviolett solution in 50% ethanol to count virus plaques. Results shown in FIG. 9 demonstrate that EMCV replication is rather ineffective in NC5T11 cells and that it is highly sensitive to interferon treatment before infection. At 8 IU/ml no viable virus can be recovered from the culture. In contrast virus replication in NC5T11#34 is only slightly affected by interferon treatment. Moreover, even in the absence of exogenous IFN, higher titers are observed for NC5T11#34. The phenomena shown model typical vaccine processes because many vaccine strains induce an IFN response in producer cells with an intact IFN pathway, infection at a low multiplicity of infection (MOI) preferred in production processes can cause IFN secretion resulting in a block of virus replication of cells that did not get infected initially. Therefore, expression of PIX may allow for high titer virus production starting with low MOI.

Example 8

Stimulation of Protein Production by pIX-RARA

NC5T11puro#8pIXRARA carrying vector F67 as well as alpha-1-antitrypsin were compared to the starter clone NC5T11puro#8 in there capacity to produce alpha-1 antitrypsin in a shaker batch assay. Cells were seeded in EXCELL VPRO (JRH Biosciences) at $6 \times 10^4$ cells/ml in 50 ml polypropylene shaker tubes (TPP, Switzerland) with a total volume of 12 ml and subjected to rotation with a radius of 1 cm and a speed of 160 rpm. Culture was continued until day 22. Besides suspension cells, a ring of cell clusters adhering to the tube wall was formed. The cells in these clusters preserved a viability above 70% throughout the process. Because dissociation of these clusters by Trypsin or Acutase (PAA) was not successful, growth kinetics and maximal cell densities were not determined. Samples were taken at day 9, 13, and 22 and titers were determined using the alpha-1-antitrypsin ELISA. Results are shown in FIG. 10.

Example 9

Generation of Duck Retina Cells Expressing pIX

The cell line CR, derived from primary duck retina cells and immortalized according to defined risk guidelines is described elsewhere (patent application WO05042728, plasmid 60E-transfected retina cells). The cells were cultivated in DMEM:F12 medium (Invitrogen, Carlsbad, Calif. 92008, USA) supplemented to 5% fetal calf serum (Biochrom AG, 12213 Berlin, Germany) at 39° C. and 7.5% $CO_2$. For passaging, the cells were briefly treated with TrypLE Express (Invitrogen). Plasmid 76F pEFPIX1 was linearized with Ssp I and Xmn I restriction enzymes (both from New England Biolabs, Beverly, Mass. 01915-5599, USA) and purified to 400 ng/μl by affinity chromatography (gel extraction kit from Qiagen, 40724 Hilden, Germany). 5 μl (2 μg) of the purified DNA was transfected into CR cells with the Effectene reagents (Qiagen): DNA was mixed with 16 μl Enhancer and 200 μl EC Buffer. After 2 min at room temperature, 18 μl Effectene were added and liposome formation allowed for 10 min at room temperature. The transfection mix was added to 1 ml culture volume on cells seeded to 80% confluency in 6-well plates on the previous day. High transfection efficiency was confirmed with a parallel transfection of pEGFP-N1 (Clontech, Palo Alto, Calif. 94303-4230, USA).

The pIX-transfected cultures were expanded into T75 flasks three days after transfection and selection was initiated with 25 μg/ml hygromycin B (Invitrogen). Medium was replaced once per week with hygromycin B raised to 50 μg/ml. After three weeks, a total of four large foci survived and were re-seeded into a T25 flask: cells were detached with TrypLE and collected with 100×g for 10 min, resuspended in fresh medium and plated into a T25 flask.

Four weeks after transfection, cells from a healthy, sub-confluent culture in a T25 flask were detached with TrypLE into 5 ml of DMEM:F12, 5% FCS. 2 ml thereof were mixed with medium #63032-1000M (JRH Biosciences, KS 66215, USA) a medium free of animal-derived components intended for maintenance of suspension cultures. Hygromycin B was added to 50 μg/ml. Genomic DNA was isolated from 2 ml of the culture and subjected to PCR against the pIX transgene with primers V293 and V294. Negative control was provided by a parallel reaction without DNA, positive control by a parallel reaction with plasmid 76F. The expected PCR product in FIG. 11 (left panel) demonstrates stable insertion of the pIX transgene into the CR cells, now termed "CRpIX".

Expression of the PIX protein was confirmed by Western blotting: $6×10^5$ cells were disrupted by boiling in (20 mM Tris pH 7.4, 300 mM NaCl, 1% Na-desoxycholat, 1% Triton® X-100, 0.1% SDS) and protein was separated by gel electrophoresis, then transferred to a nylon membrane. PIX was detected with pIX primary antibody (a generous gift from Dr. W. Seidel, Ernst-Moritz-Arndt-Universität Greifswald, Germany), then reacted with secondary antibody directed against the former antibody and labeled with alkaline phosphatase.

The signal of expected size in FIG. 11 (right panel) confirms expression of pIX in CRpIX cells. No signal was present in the negative control from 293 cells prepared in a parallel reaction.

The cells were cultivated in medium #63032-1000M for two additional passages, then transferred to medium #14561-1000M (also from JRH Biosciences) for two additional passages. All JRH media were supplemented to 1× with Glutamax I (Invitrogen) and 100 μg/ml hygromycin B.

With the second passage in medium #14561-1000M a small fraction (approx. 2% of a 5 ml suspension culture) was resuspended thoroughly into DMEM:F12, FCS medium and plated into a 15 cm-diameter petri dish with. After 6 days, eleven foci were removed to individual cavities of a 12-well plate and maintained in DMEM:F12, FCS medium. For clone transfer, the medium was aspirated and cloning disks (Sigma, Mo., USA) soaked in TrypLE, briefly applied directly to the clones, then transferred to the cavities filled with medium. Individual clones were expanded for further experiments and determination of growth properties.

To analyze maintenance of PIX in the stably transfected cells genomic DNA was isolated from $1×10^6$ cells with the QIAamp DNA Blood kit (Qiagen) and number of E1B and PIX molecules was determined in 25 ng and 50 ng of genomic DNA in an ABI 7000 TaqMan reaction with SYBR Green (ABI) detection chemistry. Primers used for quantification were gTggTTgCTTCATgCTAgTg (SEQ ID NO:13) and TCTTCAgCAggTgACAgTTg (SEQ ID NO:14) for E1B, ACCTACgAgACCgTgTCTg (SEQ ID NO:15) and gAgC-CgTCAACTTgTCATC (SEQ ID NO:16) for PIX. As E1B was introduced independently and must be maintained for the cells to survive this gene serves as an internal marker to standardize PIX copy number and gene expression strength.

FIG. 12 demonstrates stable maintenance of PIX transgene in CR suspension cells even in absence of selection pressure. It also demonstrates that PIX-positive cells suffer from a decrease in growth rate. We consistently observed decreased proliferation for all of our cells (avian and human cells) upon stable transfection with a PIX-expression plasmid demonstrating an impact of PIX on the biochemistry of the host cell. Furthermore, we observed a tendency in PIX-positive, adherent CR cells to avoid growth into confluent layers (increased contact inhibition).

Example 10

Generation of Duck Somite Cells Expressing pIX

The cell line CS is derived from embryonal somites, also described in patent application WO05042728. Generation of PIX-positive CS cells was performed in parallel to the above described procedure for the CR line. Contrary to CRpIX, no suspension cultures were established for CSpIX. Strict anchorage dependency is a feature of the CS cells. A cell that does not proliferate in suspension can be considered to be less tumorigenic as the potential to metastasize is severely impaired. PIX protein does not change this property in CS cells. Although pleotropic this protein therefore appears not to impact on the transformation phenotype. This observation supports our assumption that PIX can safely be applied in biopharmaceutical processes.

Example 11

PIX Effect on MVA Replication in CS Cells

CS cells stably transfected for PIX expression and parental CS cells as reference were seeded into a 6-well plate at $2×10^6$ cells/cavity and infected with Modified Vaccinia Ankara virus (MVA) at an m.o.i. of 0.1 on the following day. Pictures to document the differences in the advance of CPE were taken 48 h and 72 h post infection. Virus yield in the supernatant 48 h post infection and complete yield (supernatant together with lysed cell pellet) 72 h post infection was determined in a microfocus assay. The results are shown in FIG. 13: the presence of PIX in the CS cells appears to delay the onset of CPE at 48 h post infection when compared to the parental reference. 72 h post infection both cultures are lysed completely suggesting that the differences in the extent of CPE is not due to a mixture of MVA-refractory and MVA-susceptible cells in the CS.PIX population.

To our knowledge, no PIX-positive cell has ever been tested against viruses other than cognate adenovirus.

Example 12

PIX Effect on MVA Replication in CR Cells

The positive effect of the PIX protein was also quantified on CR cells. Contrary to CS cells, the CR cells are adapted to suspension. Suspension cultures are preferred for many industrial applications. We therefore determined the PIX effect in such a system as opposed to adherent culture.

For CR cells the PIX-supportive effect is not as pronounced as in CS cells but we consistently observe higher titers for MVA. MVA yields were optimized in a series of experiments and found to be greatest 48 h post infection at medium cell densities. FIG. 14 shows a comparison of suspension clone CR.HS (selected out of several clones as the cell line with greatest MVA yields) and PIX(+) cell line CR.MCX. The abscissa indicates m.o.i. (0.01, 0.05 or 0.1, respectively), the ordinate indicates burst and the size of the bubbles indicates cell densities (8, 2, or 0.8×10$^6$ cells/ml, respectively). Burst is the ration of output virus (or yield) to input virus (the inoculum dependent on cell number and m.o.i.) and thus a measurement of amplification efficiency. In all configurations, the PIX(+) cell lines exceeds the PIX(−) line in performance.

Example 13

Nuclear Exclusion of PIX

A PIX-GFP fusion gene was generated to visualize distribution of the PIX protein in life cells and to overcome weak binding activity of the available antibody: Plasmid 76F pEF-PIX1 was treated with Acc I and Dra I restriction enzymes and termini were blunted with Klenow polymerase (all from New England Biolabs, Beverly, Mass. 01915-5599, USA). Out of the complex banding pattern, the desired fragment of 447 bp containing the PIX coding sequence was isolated by agarose gel extraction (gel extraction kit from Qiagen, 40724 Hilden, Germany). The Dra I restriction enzyme recognizes the sequence "ttTAAa" to cut after the last thymidine residue, wherein the central "TAA" triplett is the stop codon of the PIX open reading frame. The 447 bp fragment therefore is devoid of a stop codon. Fusion of this fragment to the gene for EGFP in the plasmid pEGFP-N1 opened with Sma I (also New England Biolabs) generates a continuos fusion gene of PIX followed by EGFP. The resulting plasmid was named p9GFP, the expressed fusion protein will be named PIX-GFP in this text.

CS and CR cells were transfected with p9GFP and selected with 300 μg/mL geneticin (Invitrogen) for stable PIX-GFP expression. Two populations of different PIX-GFP expression were observed within 2 weeks: one population had usually 2 to 5 bright spots of PIX-GFP in the cytoplasm, the other population had a more uniform expression of PIX-GFP in the cytoplasm and more diffuse accumulation of GFP signal in a region proximal to the nucleus. In both cases, the cell nuclei appeared as a dark region suggesting that no or very little chimeric protein enters the nucleus. Representative examples for both types of clones in CRpIXGFP are shown in FIG. 15.

Consistent with this result we found a nuclear export sequence in the PIX open reading frame by applying the search algorithm NetNES (Cour et al., Protein Eng. Des. Sel. 17, 527-536 (2004)) to the PIX primary sequence. The NES identified by this program is 313-GCACAATTGGATTCTTTGACCCGGGAACTT-342 (SEQ ID NO:17) (translated: AQLDSLTREL; SEQ ID NO:18). To our knowledge, it is the first time that such a signal has been described in the PIX protein. Conversely, a nuclear localisation sequence (NLS) has not been described in the literature for PIX and we cannot detect such a signal (for example, using the algorithm provided by the Columbia University at web site cubic.bioc.columbia.edu/cgi/var/nair/resonline.pl).

The cytoplasmic localisation of PIX-GFP in our duck cells therefore is consistent with the primary sequence of PIX.

Example 14

PIX GFP Fusion Variants

The surprising nuclear exclusion of PIX GFP was investigated with additional PIX-fusion constructs. A PIX-GFP-NLS expression plasmid was derived from the above described p9GFP construct by insertion of synthetic oligonucleotides i185 and i186. These oligos were denatured at 80° C. for 5 min and allowed to anneal in 10 mM MgCl$_2$ by gradual cooling to room temperature to yield:

```
                                        (SEQ ID NO: 19)
5'-GATGTACAAAGATCCGAAGAAGAACCGCAAAGGTTAA
CGCGGCCGCAC-3'

(SEQ ID NO: 20)
3'-CTACATGTTTCTAGGCTTCTTCTTGGCGTTTCCAATT
GCGCCGGCGTG-5'
```

This double stranded oligonucleotide was digested with BsrG I and Not I and inserted into the same sites of p9GFP. Translated, the insertion adds a NLS sequence (PKKNRK; SEQ ID NO:21) to the PIX-GFP fusion protein that resembles the simian virus 40 NLS. A new Hpa I site introduced with this insert serves as diagnostic marker to confirm successful cloning. The resulting plasmid is called p9 GFP NLS, the expressed protein PIX-GFP-NLS and the open reading frame coding for the protein PIX-GFP-NLS are shown in SEQ ID NOs:23 and 22, respectively.

A GFP-tagged PIX-RARA fusion protein was generated via PCR amplification of a fragment containing PIX-RARA with primers EBR 44A (5'-GGATCCTTCCTC-CTCGGGCGGGTGT-3'; SEQ ID ND:24), V293 (5'-AAC-CAGCGCTACCATGAGCACCAACTCGT 3'; SEQ ID ND:25) and plasmid #67F pEF PIX RARA NEO as template. The amplicon of 1926 bp was treated with polynucleotide kinase and inserted into pEGFP-C2 (Clontech) linearized with EcoR I and blunted with Klenow enzyme (all enzymes from New England Biolabs). The resulting plasmid is called p9 GFP RARA, the expressed protein PIX GFP RARA.

FIG. 16 shows the intracellular distribution of the various GFP-tagged proteins in transiently transfected CHO cells.

Example 15

PIX and Interferon

Many viruses induce the innate cellular immune response via TLR-3 (toll like receptor 3). TLR-3 recognizes double stranded RNA, a hallmark pattern of viral replication. Among the functions of TLR-3 is activation of NFkB and type I interferon (Alexopoulou et al., Nature 413, 732-738 (2001)). Interferon mediates an antiviral state in the host cell. The effect of interferon induction via an artificial double stranded RNA, poly I:poly C (polyinosinic-polycytidylic acid, Sigma) was examined. Surprisingly the CR and CRpIX cells displayed very little poly I:poly C sensitivity whereas CS cells clearly responded to the inductor. Unexpectedly, PIX-positive CS cells responded faster and at lower concentrations than parental CS cells (FIG. 17). To our knowledge, a connection between PIX and interferon has not been described in the current literature.

The PIX-supportive effect for MVA was stronger in CS cells than CR cells, and the CS cells responded to double stranded RNA surrogate better than CR cells. It is known that MVA induces interferon and that this virus also is equipped with proteins that alleviate the interferon response. The effect of poly I:poly C inductor on MVA in CRp9GFP and CSp9GFP cells therefore determined. FIG. 18 suggests that MVA infected cells suffer less from poly I:poly C than uninfected control. This observation is consistent with the fact that MVA both induces and interferes with the cellular innate immune response and connects with our unexpected observation that PIX from a human adenovirus in avian cells cooperates with antiviral proteins of a highly attenuated pox virus to increase yields of the latter virus.

Sequence Listing—Free Text

| SEQ ID NO | Description |
|---|---|
| 1, 2 | adenoviral pIX protein |
| 3, 4 | fusion protein pIX-RARA; |
| 5 | Ad5 E1A + E1B |
| 6-11 | primer |
| 12 | "short" human translation elongation factor 2 promoter |
| 13-16 | primer |
| 17-18 | NES |
| 19-20 | synthetic oligonucleotides encoding NLS |
| 21 | NLS |
| 22-23 | fusion protein pIX-GFP-NLS |
| 24-25 | primer |

The invention claimed is:

1. An isolated CR.PIX (17a11b) cell, deposited with the DSMZ under accession number DSM ACC2749.

2. The isolated CR.PIX (17a11b) cell of claim 1, wherein the cell further comprises a non-adenoviral target virus, a nucleic acid vector encoding a non-adenoviral target virus, or a nucleic acid vector encoding a non-adenoviral target protein.

3. The isolated CR.PIX (17a11b) cell of claim 2, wherein the cell comprises a non-adenoviral target virus, and wherein the non-adenoviral target virus is selected from the group consisting of a wild type, mutated, or deleted virus, a cold adapted or attenuated virus, vaccine strains, viral vectors carrying heterologous gene(s), lentivirus, poxvirus, fowlpox virus, canarypox virus, and adeno associated virus (aav).

4. A method for preparing a non-adenoviral target virus, comprising:
 (a) culturing the cell of claim 2 comprising the non-adenoviral target virus, and
 (b) isolating the target virus.

5. A method for preparing a non-adenoviral target protein, comprising:

(a) culturing the cell of claim 2, wherein the cell comprises the nucleic acid vector encoding the non-adenoviral target protein under conditions suitable for expressing the non-adenoviral target protein; and
(b) isolating the non-adenoviral target protein.

\* \* \* \* \*

```
                              SEQUENCE LISTING

<160> NUMBER OF SEQ ID NOS: 25

<210> SEQ ID NO 1
<211> LENGTH: 423
<212> TYPE: DNA
<213> ORGANISM: human Adenovirus serotype 5
<220> FEATURE:
<221> NAME/KEY: CDS
<222> LOCATION: (1)..(423)

<400> SEQUENCE: 1 atg agc acc aac tcg ttt gat gga agc att gtg agc tca tat ttg aca       48
Met Ser Thr Asn Ser Phe Asp Gly Ser Ile Val Ser Ser Tyr Leu Thr
1               5                   10                  15 acg cgc atg ccc cca tgg gcc ggg gtg cgt cag aat gtg atg ggc tcc       96
Thr Arg Met Pro Pro Trp Ala Gly Val Arg Gln Asn Val Met Gly Ser
            20                  25                  30 agc att gat ggt cgc ccc gtc ctg ccc gca aac tct act acc ttg acc      144
Ser Ile Asp Gly Arg Pro Val Leu Pro Ala Asn Ser Thr Thr Leu Thr
        35                  40                  45 tac gag acc gtg tct gga acg ccg ttg gag act gca gcc tcc gcc gcc      192
Tyr Glu Thr Val Ser Gly Thr Pro Leu Glu Thr Ala Ala Ser Ala Ala
    50                  55                  60 gct tca gcc gct gca gcc acc gcc cgc ggg att gtg act gac ttt gct      240
Ala Ser Ala Ala Ala Ala Thr Ala Arg Gly Ile Val Thr Asp Phe Ala
65                  70                  75                  80 ttc ctg agc ccg ctt gca agc agt gca gct tcc cgt tca tcc gcc cgc      288
Phe Leu Ser Pro Leu Ala Ser Ser Ala Ala Ser Arg Ser Ser Ala Arg
                85                  90                  95 gat gac aag ttg acg gct ctt ttg gca caa ttg gat tct ttg acc cgg      336
Asp Asp Lys Leu Thr Ala Leu Leu Ala Gln Leu Asp Ser Leu Thr Arg
            100                 105                 110 gaa ctt aat gtc gtt tct cag cag ctg ttg gat ctg cgc cag cag gtt      384
Glu Leu Asn Val Val Ser Gln Gln Leu Leu Asp Leu Arg Gln Gln Val
        115                 120                 125 tct gcc ctg aag gct tcc tcc cct ccc aat gcg gtt taa                  423
Ser Ala Leu Lys Ala Ser Ser Pro Pro Asn Ala Val
    130                 135                 140

<210> SEQ ID NO 2
<211> LENGTH: 140
<212> TYPE: PRT
<213> ORGANISM: human Adenovirus serotype 5

<400> SEQUENCE: 2

Met Ser Thr Asn Ser Phe Asp Gly Ser Ile Val Ser Ser Tyr Leu Thr
1               5                   10                  15
```

```
Thr Arg Met Pro Pro Trp Ala Gly Val Arg Gln Asn Val Met Gly Ser
            20                  25                  30

Ser Ile Asp Gly Arg Pro Val Leu Pro Ala Asn Ser Thr Thr Leu Thr
        35                  40                  45

Tyr Glu Thr Val Ser Gly Thr Pro Leu Glu Thr Ala Ala Ser Ala Ala
    50                  55                  60

Ala Ser Ala Ala Ala Thr Ala Arg Gly Ile Val Thr Asp Phe Ala
65                  70                  75                  80

Phe Leu Ser Pro Leu Ala Ser Ser Ala Ala Ser Arg Ser Ser Ala Arg
                85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Pro Asn Ala Val
    130                 135                 140

<210> SEQ ID NO 3
<211> LENGTH: 1635
<212> TYPE: DNA
<213> ORGANISM: Artificial
<220> FEATURE:
<223> OTHER INFORMATION: Synthetic fusion protein pIX-RARA
<220> FEATURE:
<221> NAME/KEY: CDS
<222> LOCATION: (1)..(1635)

<400> SEQUENCE: 3
```

| | | | | | | | | | | | | | | | | |
|---|---|---|---|---|---|---|---|---|---|---|---|---|---|---|---|---|
| atg | agc | acc | aac | tcg | ttt | gat | gga | agc | att | gtg | agc | tca | tat | ttg | aca | 48 |
| Met | Ser | Thr | Asn | Ser | Phe | Asp | Gly | Ser | Ile | Val | Ser | Ser | Tyr | Leu | Thr | |
| 1 | | | | 5 | | | | | 10 | | | | | 15 | | |

```
acg cgc atg ccc cca tgg gcc ggg gtg cgt cag aat gtg atg ggc tcc       96
Thr Arg Met Pro Pro Trp Ala Gly Val Arg Gln Asn Val Met Gly Ser
            20                  25                  30 agc att gat ggt cgc ccc gtc ctg ccc gca aac tct act acc ttg acc      144
Ser Ile Asp Gly Arg Pro Val Leu Pro Ala Asn Ser Thr Thr Leu Thr
        35                  40                  45 tac gag acc gtg tct gga acg ccg ttg gag act gca gcc tcc gcc gcc      192
Tyr Glu Thr Val Ser Gly Thr Pro Leu Glu Thr Ala Ala Ser Ala Ala
    50                  55                  60 gct tca gcc gct gca gcc acc gcc cgc ggg att gtg act gac ttt gct      240
Ala Ser Ala Ala Ala Thr Ala Arg Gly Ile Val Thr Asp Phe Ala
65                  70                  75                  80 ttc ctg agc ccg ctt gca agc agt gca gct tcc cgt tca tcc gcc cgc      288
Phe Leu Ser Pro Leu Ala Ser Ser Ala Ala Ser Arg Ser Ser Ala Arg
                85                  90                  95 gat gac aag ttg acg gct ctt ttg gca caa ttg gat tct ttg acc cgg      336
Asp Asp Lys Leu Thr Ala Leu Leu Ala Gln Leu Asp Ser Leu Thr Arg
            100                 105                 110 gaa ctt aat gtc gtt tct cag cag ctg ttg gat ctg cgc cag cag gtt      384
Glu Leu Asn Val Val Ser Gln Gln Leu Leu Asp Leu Arg Gln Gln Val
        115                 120                 125 tct gcc ctg aag gct tcc tcc cct ccc aat gcg gtt gcc acc att gag      432
Ser Ala Leu Lys Ala Ser Ser Pro Pro Asn Ala Val Ala Thr Ile Glu
    130                 135                 140 acc cag agc agc agt tct gaa gag ata gtg ccc agc cct ccc tcg cca      480
Thr Gln Ser Ser Ser Glu Glu Ile Val Pro Ser Pro Pro Ser Pro
145                 150                 155                 160 ccc cct cta ccc cgc atc tac aag cct tgc ttt gtc tgt cag gac aag      528
Pro Pro Leu Pro Arg Ile Tyr Lys Pro Cys Phe Val Cys Gln Asp Lys
```

|     |     |
| --- | --- |
| tcc tca ggc tac cac tat ggg gtc agc gcc tgt gag ggc tgc aag ggc<br>Ser Ser Gly Tyr His Tyr Gly Val Ser Ala Cys Glu Gly Cys Lys Gly<br>           180                     185                     190 | 576 |
| ttc ttc cgc cgc agc atc cag aag aac atg gtg tac acg tgt cac cgg<br>Phe Phe Arg Arg Ser Ile Gln Lys Asn Met Val Tyr Thr Cys His Arg<br>          195                     200                     205 | 624 |
| gac aag aac tgc atc atc aac aag gtg acc cgg aac cgc tgc cag tac<br>Asp Lys Asn Cys Ile Ile Asn Lys Val Thr Arg Asn Arg Cys Gln Tyr<br>210                     215                     220 | 672 |
| tgc cga ctg cag aag tgc ttt gaa gtg ggc atg tcc aag gag tct gtg<br>Cys Arg Leu Gln Lys Cys Phe Glu Val Gly Met Ser Lys Glu Ser Val<br>225                   230                     235                     240 | 720 |
| aga aac gac cga aac aag aag aag aag gag gtg ccc aag ccc gag tgc<br>Arg Asn Asp Arg Asn Lys Lys Lys Lys Glu Val Pro Lys Pro Glu Cys<br>                   245                     250                     255 | 768 |
| tct gag agc tac acg ctg acg ccg gag gtg ggg gag ctc att gag aag<br>Ser Glu Ser Tyr Thr Leu Thr Pro Glu Val Gly Glu Leu Ile Glu Lys<br>                 260                     265                     270 | 816 |
| gtg cgc aaa gcg cac cag gaa acc ttc cct gcc ctc tgc cag ctg ggc<br>Val Arg Lys Ala His Gln Glu Thr Phe Pro Ala Leu Cys Gln Leu Gly<br>          275                     280                     285 | 864 |
| aaa tac act acg aac aac agc tca gaa caa cgt gtc tct ctg gac att<br>Lys Tyr Thr Thr Asn Asn Ser Ser Glu Gln Arg Val Ser Leu Asp Ile<br>290                     295                     300 | 912 |
| gac ctc tgg gac aag ttc agt gaa ctc tcc acc aag tgc atc att aag<br>Asp Leu Trp Asp Lys Phe Ser Glu Leu Ser Thr Lys Cys Ile Ile Lys<br>305                   310                     315                     320 | 960 |
| act gtg gag ttc gcc aag cag ctg ccc ggc ttc acc acc ctc acc atc<br>Thr Val Glu Phe Ala Lys Gln Leu Pro Gly Phe Thr Thr Leu Thr Ile<br>                   325                     330                     335 | 1008 |
| gcc gac cag atc acc ctc ctc aag gct gcc tgc ctg gac atc ctg atc<br>Ala Asp Gln Ile Thr Leu Leu Lys Ala Ala Cys Leu Asp Ile Leu Ile<br>                   340                     345                     350 | 1056 |
| ctg cgg atc tgc acg cgg tac acg ccc gag cag gac acc atg acc ttc<br>Leu Arg Ile Cys Thr Arg Tyr Thr Pro Glu Gln Asp Thr Met Thr Phe<br>          355                     360                     365 | 1104 |
| tcg gac ggg ctg acc ctg aac cgg acc cag atg cac aac gct ggc ttc<br>Ser Asp Gly Leu Thr Leu Asn Arg Thr Gln Met His Asn Ala Gly Phe<br>370                     375                     380 | 1152 |
| ggc ccc ctc acc gac ctg gtc ttt gcc ttc gcc aac cag ctg ctg ccc<br>Gly Pro Leu Thr Asp Leu Val Phe Ala Phe Ala Asn Gln Leu Leu Pro<br>385                   390                     395                     400 | 1200 |
| ctg gag atg gat gat gcg gag acg ggg ctg ctc agc gcc atc tgc ctc<br>Leu Glu Met Asp Asp Ala Glu Thr Gly Leu Leu Ser Ala Ile Cys Leu<br>                   405                     410                     415 | 1248 |
| atc tgc gga gac cgc cag gac ctg gag cag ccg gac cgg gtg gac atg<br>Ile Cys Gly Asp Arg Gln Asp Leu Glu Gln Pro Asp Arg Val Asp Met<br>                   420                     425                     430 | 1296 |
| ctg cag gag ccg ctg ctg gag gcg cta aag gtc tac gtg cgg aag cgg<br>Leu Gln Glu Pro Leu Leu Glu Ala Leu Lys Val Tyr Val Arg Lys Arg<br>          435                     440                     445 | 1344 |
| agg ccc agc cgc ccc cac atg ttc ccc aag atg cta atg aag att act<br>Arg Pro Ser Arg Pro His Met Phe Pro Lys Met Leu Met Lys Ile Thr<br>450                     455                     460 | 1392 |
| gac ctg cga agc atc agc gcc aag ggg gct gag cgg gtg atc acg ctg<br>Asp Leu Arg Ser Ile Ser Ala Lys Gly Ala Glu Arg Val Ile Thr Leu<br>465                     470                     475                     480 | 1440 |
| aag atg gag atc ccg ggc tcc atg ccg cct ctc atc cag gaa atg ttg<br> | 1488 |

```
Lys Met Glu Ile Pro Gly Ser Met Pro Pro Leu Ile Gln Glu Met Leu
            485                 490                 495
gag gac tca gag ggc ctg gac act ctg agc gga cag ccg ggg ggt ggg      1536
Glu Asp Ser Glu Gly Leu Asp Thr Leu Ser Gly Gln Pro Gly Gly Gly
            500                 505                 510
ggg cgg gac ggg ggt ggc ctg gcc ccc ccg cca ggc agc tgt agc ccc      1584
Gly Arg Asp Gly Gly Gly Leu Ala Pro Pro Pro Gly Ser Cys Ser Pro
            515                 520                 525
agc ctc agc ccc agc tcc aac aga agc agc ccg gcc acc cac tcc ccg      1632
Ser Leu Ser Pro Ser Ser Asn Arg Ser Ser Pro Ala Thr His Ser Pro
        530                 535                 540
tga                                                                   1635
```

<210> SEQ ID NO 4
<211> LENGTH: 544
<212> TYPE: PRT
<213> ORGANISM: Artificial
<220> FEATURE:
<223> OTHER INFORMATION: Synthetic Construct

<400> SEQUENCE: 4

```
Met Ser Thr Asn Ser Phe Asp Gly Ser Ile Val Ser Ser Tyr Leu Thr
1               5                   10                  15

Thr Arg Met Pro Pro Trp Ala Gly Val Arg Gln Asn Val Met Gly Ser
            20                  25                  30

Ser Ile Asp Gly Arg Pro Val Leu Pro Ala Asn Ser Thr Thr Leu Thr
        35                  40                  45

Tyr Glu Thr Val Ser Gly Thr Pro Leu Glu Thr Ala Ala Ser Ala Ala
    50                  55                  60

Ala Ser Ala Ala Ala Thr Ala Arg Gly Ile Val Thr Asp Phe Ala
65                  70                  75                  80

Phe Leu Ser Pro Leu Ala Ser Ala Ala Ser Arg Ser Ser Ala Arg
                85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Asn Ala Val Ala Thr Ile Glu
    130                 135                 140

Thr Gln Ser Ser Ser Ser Glu Glu Ile Val Pro Ser Pro Ser Pro
145                 150                 155                 160

Pro Pro Leu Pro Arg Ile Tyr Lys Pro Cys Phe Val Cys Gln Asp Lys
                165                 170                 175

Ser Ser Gly Tyr His Tyr Gly Val Ser Ala Cys Glu Gly Cys Lys Gly
            180                 185                 190

Phe Phe Arg Arg Ser Ile Gln Lys Asn Met Val Tyr Thr Cys His Arg
        195                 200                 205

Asp Lys Asn Cys Ile Ile Asn Lys Val Thr Arg Asn Arg Cys Gln Tyr
    210                 215                 220

Cys Arg Leu Gln Lys Cys Phe Glu Val Gly Met Ser Lys Glu Ser Val
225                 230                 235                 240

Arg Asn Asp Arg Asn Lys Lys Lys Glu Val Pro Lys Pro Glu Cys
                245                 250                 255

Ser Glu Ser Tyr Thr Leu Thr Pro Glu Val Gly Glu Leu Ile Glu Lys
            260                 265                 270

Val Arg Lys Ala His Gln Glu Thr Phe Pro Ala Leu Cys Gln Leu Gly
```

```
                275                 280                 285
Lys Tyr Thr Thr Asn Asn Ser Ser Glu Gln Arg Val Ser Leu Asp Ile
        290                 295                 300
Asp Leu Trp Asp Lys Phe Ser Glu Leu Ser Thr Lys Cys Ile Ile Lys
305                 310                 315                 320
Thr Val Glu Phe Ala Lys Gln Leu Pro Gly Phe Thr Thr Leu Thr Ile
                325                 330                 335
Ala Asp Gln Ile Thr Leu Leu Lys Ala Ala Cys Leu Asp Ile Leu Ile
        340                 345                 350
Leu Arg Ile Cys Thr Arg Tyr Thr Pro Glu Gln Asp Thr Met Thr Phe
            355                 360                 365
Ser Asp Gly Leu Thr Leu Asn Arg Thr Gln Met His Asn Ala Gly Phe
        370                 375                 380
Gly Pro Leu Thr Asp Leu Val Phe Ala Phe Ala Asn Gln Leu Leu Pro
385                 390                 395                 400
Leu Glu Met Asp Asp Ala Glu Thr Gly Leu Leu Ser Ala Ile Cys Leu
                405                 410                 415
Ile Cys Gly Asp Arg Gln Asp Leu Glu Gln Pro Asp Arg Val Asp Met
            420                 425                 430
Leu Gln Glu Pro Leu Leu Glu Ala Leu Lys Val Tyr Val Arg Lys Arg
        435                 440                 445
Arg Pro Ser Arg Pro His Met Phe Pro Lys Met Leu Met Lys Ile Thr
    450                 455                 460
Asp Leu Arg Ser Ile Ser Ala Lys Gly Ala Glu Arg Val Ile Thr Leu
465                 470                 475                 480
Lys Met Glu Ile Pro Gly Ser Met Pro Pro Leu Ile Gln Glu Met Leu
                485                 490                 495
Glu Asp Ser Glu Gly Leu Asp Thr Leu Ser Gly Gln Pro Gly Gly Gly
            500                 505                 510
Gly Arg Asp Gly Gly Gly Leu Ala Pro Pro Pro Gly Ser Cys Ser Pro
        515                 520                 525
Ser Leu Ser Pro Ser Ser Asn Arg Ser Ser Pro Ala Thr His Ser Pro
    530                 535                 540
```

<210> SEQ ID NO 5
<211> LENGTH: 3069
<212> TYPE: DNA
<213> ORGANISM: human Adenovirus serotype 5

<400> SEQUENCE: 5

```
ttatagtcag ctgacgtgta gtgtatttat acccggtgag ttcctcaaga ggccactctt    60
gagtgccagc gagtagagtt ttctcctccg agccgctccg acaccgggac tgaaaatgag   120
acatattatc tgccacggag gtgttattac cgaagaaatg ccgccagtc ttttggacca   180
gctgatcgaa gaggtactgg ctgataatct tccacctcct agccattttg aaccacctac   240
ccttcacgaa ctgtatgatt tagacgtgac ggcccccgaa gatcccaacg aggaggcggt   300
ttcgcagatt tttcccgact ctgtaatgtt ggcggtgcag gaagggattg acttactcac   360
ttttccgccg cgcccggtt ctccggagcc gcctcacctt tcccggcagc ccgagcagcc   420
ggagcagaga gccttgggtc cggtttctat gccaaaccct gtaccggagg tgatcgatct   480
tacctgccac gaggctggct ttccacccag tgacgacgag gatgaagagg gtgaggagtt   540
tgtgttagat tatgtggagc accccgggca cggttgcagg tcttgtcatt atcaccggag   600
gaatacgggg gacccagata ttatgtgttc gctttgctat atgaggacct gtggcatgtt   660
```

```
tgtctacagt aagtgaaaat tatgggcagt gggtgataga gtggtgggtt tggtgtggta        720
attttttttt taattttttac agttttgtgg tttaaagaat tttgtattgt gattttttta        780
aaaggtcctg tgtctgaacc tgagcctgag cccgagccag aaccggagcc tgcaagacct        840
acccgccgtc ctaaaatggc gcctgctatc ctgagacgcc cgacatcacc tgtgtctaga        900
gaatgcaata gtagtacgga tagctgtgac tccggtcctt ctaacacacc tcctgagata        960
cacccggtgg tcccgctgtg ccccattaaa ccagttgccg tgagagttgg tgggcgtcgc       1020
caggctgtgg aatgtatcga ggacttgctt aacgagcctg ggcaaccttt ggacttgagc       1080
tgtaaacgcc ccaggccata aggtgtaaac ctgtgattgc gtgtgtggtt aacgcctttg       1140
tttgctgaat gagttgatgt aagtttaata aagggtgaga taatgtttaa cttgcatggc       1200
gtgttaaatg gggcggggct taagggtat ataatgcgcc gtgggctaat cttggttaca       1260
tctgacctca tggaggcttg ggagtgtttg gaagattttt ctgctgtgcg taacttgctg       1320
gaacagagct ctaacagtac ctcttggttt tggaggtttc tgtggggctc atcccaggca       1380
aagttagtct gcagaattaa ggaggattac aagtgggaat ttgaagagct tttgaaatcc       1440
tgtggtgagc tgtttgattc tttgaatctg ggtcaccagg cgcttttcca agagaaggtc       1500
atcaagactt tggattttc cacaccgggg cgcgctgcgg ctgctgttgc ttttttgagt       1560
tttataaagg ataaatggag cgaagaaacc catctgagcg gggggtacct gctggatttt       1620
ctggccatgc atctgtggag agcggttgtg agacacaaga atcgcctgct actgttgtct       1680
tccgtccgcc cggcgataat accgacgag gagcagcagc agcagcagga ggaagccagg       1740
cggcggcggc aggagcagag cccatggaac ccgagagccg gcctggaccc tcgggaatga       1800
atgttgtaca ggtggctgaa ctgtatccag aactgagacg cattttgaca attacagagg       1860
atgggcaggg gctaaagggg gtaaagaggg agcgggggc ttgtgaggct acagaggagg       1920
ctaggaatct agcttttagc ttaatgacca gacaccgtcc tgagtgtatt acttttcaac       1980
agatcaagga taattgcgct aatgagcttg atctgctggc gcagaagtat tccatagagc       2040
agctgaccac ttactggctg cagccagggg atgattttga ggaggctatt agggtatatg       2100
caaaggtggc acttaggcca gattgcaagt acaagatcag caaacttgta aatatcagga       2160
attgttgcta catttctggg aacggggccg aggtggagat agatacggag gatagggtgg       2220
cctttagatg tagcatgata aatatgtggc cgggggtgct tggcatggac ggggtggtta       2280
ttatgaatgt aaggtttact ggccccaatt ttagcggtac ggttttcctg gccaatacca       2340
accttatcct cacgggtta agcttctatg ggtttaacaa tacctgtgtg gaagcctgga       2400
ccgatgtaag ggttcggggc tgtgcctttt actgctgctg aaggggggtg gtgtgtcgcc       2460
ccaaaagcag ggcttcaatt aagaaatgcc tctttgaaag gtgtaccttg ggtatcctgt       2520
ctgagggtaa ctccagggtg cgccacaatg tggcctccga ctgtggttgc ttcatgctag       2580
tgaaaagcgt ggctgtgatt aagcataaca tggtatgtgg caactgcgag acagggcct       2640 ctcagatgct gacctgctcg acggcaact gtcacctgct gaagaccatt cacgtagcca       2700
gccactctcg caaggcctgg ccagtgtttg agcataacat actgacccgc tgttccttgc       2760
atttgggtaa caggaggggg gtgttcctac cttaccaatg caatttgagt cacactaaga       2820
tattgcttga gcccgagagc atgtccaagg tgaacctgaa cggggtgttt gacatgacca       2880
tgaagatctg gaaggtgctg aggtacgatg agacccgcac caggtgcaga ccctgcgagt       2940
gtggcggtaa acatattagg aaccagcctg tgatgctgga tgtgaccgag gagctgaggc       3000
```

```
ccgatcactt ggtgctggcc tgcacccgcg ctgagtttgg ctctagcgat gaagatacag    3060
attgaggat                                                            3069
```

<210> SEQ ID NO 6
<211> LENGTH: 29
<212> TYPE: DNA
<213> ORGANISM: Artificial
<220> FEATURE:
<223> OTHER INFORMATION: Synthetic primer

<400> SEQUENCE: 6

```
aaccagcgct accatgagca ccaactcgt                                        29
```

<210> SEQ ID NO 7
<211> LENGTH: 29
<212> TYPE: DNA
<213> ORGANISM: Artificial
<220> FEATURE:
<223> OTHER INFORMATION: Synthetic primer

<400> SEQUENCE: 7

```
aatggtggca accgcattgg gaggggagg                                        29
```

<210> SEQ ID NO 8
<211> LENGTH: 30
<212> TYPE: DNA
<213> ORGANISM: Artificial
<220> FEATURE:
<223> OTHER INFORMATION: Synthetic primer

<400> SEQUENCE: 8

```
ccaatgcggt tgccaccatt gagacccaga                                       30
```

<210> SEQ ID NO 9
<211> LENGTH: 28
<212> TYPE: DNA
<213> ORGANISM: Artificial
<220> FEATURE:
<223> OTHER INFORMATION: Synthetic primer

<400> SEQUENCE: 9

```
aaggagcgct ggcgagggct gtgtccat                                         28
```

<210> SEQ ID NO 10
<211> LENGTH: 29
<212> TYPE: DNA
<213> ORGANISM: Artificial
<220> FEATURE:
<223> OTHER INFORMATION: Synthetic primer

<400> SEQUENCE: 10

```
aaccagcgct accatgagca ccaactcgt                                        29
```

<210> SEQ ID NO 11
<211> LENGTH: 28
<212> TYPE: DNA
<213> ORGANISM: Artificial
<220> FEATURE:
<223> OTHER INFORMATION: Synthetic primer

<400> SEQUENCE: 11

```
accgagcgct tgttttaaac cgcattgg                                         28
```

<210> SEQ ID NO 12
<211> LENGTH: 1313

```
<212> TYPE: DNA
<213> ORGANISM: Homo sapiens

<400> SEQUENCE: 12
cccgagatgc ccagcttcta ttctagagcg ccgcgccggc gccgaatggg ttaacgggcg    60
gggggacacg cctccgtgcg cttgcgcggc gtcccttcgc cccgccttcg cagcgcagtc   120
acatgacccg cccaaccggc gtccgcctat aaaaagctga gtgttgacgt cagcgttctc   180
ttccgccgtc gtcgccgcca tcctcggcgc gactcgcttc tttcggttct acctgggaga   240
atccaccgcc atccgccaac gcgacagata tcaggtgagt aaccctgcct cgctggtgcc   300
ccggagcggg ggcggggcct ccgcggggcc tacgctgcct agcctgggac gctggggccc   360 ccgtgccag gaggagacgt agcggcggcg gggccggagg acccggggct ggggaagcgg    420
ccgccgccat gtctgtgccc atgtctgtgc gccgcgctgt tcaccgagcc ctttctccgt   480
ttccgagggc gccataacct tgcccagacc tggttggagc tgggttgtta gcggggatgg   540
gggtggggaa tgatgatgtg gcaggcgtag taatggcggg caccgcgtg gaagcgggga    600 gacagggagg cgccttatgt aacccgcggg ccgcgagttt gagatcgatt ttctgccggg   660
ggactagggg cggcagggaa tggcagaacg agcaaagcga cacctgaaag gctcccctt    720 tccttccaaa taccttctcc tgatgctgtt aatcgtcgac cttaggcact tgtccttcct   780
atgactccca gatgtacaaa gactcttatt gagacacgag gtgtaggctt gtggcagtta   840
gggccgttcc ggctccccgt tatttcctgg ggtgggtggc cttgtctgat cccgtttgcc   900
aaggggtgac cttgcatttt atgatgaagc ttcttgctcg gggaagtttg ggtggcccgg   960
tgacaacgtg gaggggcttt aggagagga ttcatcccctt acgtgtttgg ccccaaatga  1020
gactttagta tttgtacctg gtatcaagga aatctgttga cactcagttt tattcctgag  1080
cacttttatt tctgggttgt caatcatgaa tgacacctat taacggtggt tccttggaga  1140
ttgcggggtg gctcttaagg ggtgttaggc tggcaagatt cggtgggctt ggggcacccc  1200
agcaccaacc ccctcctggc cttgggcatg ctggttcgtt tggactgaac gctccgtgcc  1260
atgctgtgtt cctggaaatc acgagctggt ctgagcctcc ttgtcttgcc cag         1313

<210> SEQ ID NO 13
<211> LENGTH: 20
<212> TYPE: DNA
<213> ORGANISM: Artificial
<220> FEATURE:
<223> OTHER INFORMATION: Synthetic primer

<400> SEQUENCE: 13
gtggttgctt catgctagtg                                                20

<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
tcttcagcag gtgacagttg                                                20

<210> SEQ ID NO 15
<211> LENGTH: 19
<212> TYPE: DNA
<213> ORGANISM: Artificial
<220> FEATURE:
```

```
<223> OTHER INFORMATION: Synthetic primer

<400> SEQUENCE: 15
acctacgaga ccgtgtctg                                              19

<210> SEQ ID NO 16
<211> LENGTH: 19
<212> TYPE: DNA
<213> ORGANISM: Artificial
<220> FEATURE:
<223> OTHER INFORMATION: Synthetic primer

<400> SEQUENCE: 16
gagccgtcaa cttgtcatc                                              19

<210> SEQ ID NO 17
<211> LENGTH: 30
<212> TYPE: DNA
<213> ORGANISM: Artificial
<220> FEATURE:
<223> OTHER INFORMATION: Synthetic NES sequence

<400> SEQUENCE: 17
gcacaattgg attctttgac ccgggaactt                                  30

<210> SEQ ID NO 18
<211> LENGTH: 10
<212> TYPE: PRT
<213> ORGANISM: Artificial
<220> FEATURE:
<223> OTHER INFORMATION: Synthetic NES sequence

<400> SEQUENCE: 18

Ala Gln Leu Asp Ser Leu Thr Arg Glu Leu
1               5                   10

<210> SEQ ID NO 19
<211> LENGTH: 48
<212> TYPE: DNA
<213> ORGANISM: Artificial
<220> FEATURE:
<223> OTHER INFORMATION: Synthetic NLS sequence

<400> SEQUENCE: 19
gatgtacaaa gatccgaaga agaaccgcaa aggttaacgc ggccgcac              48

<210> SEQ ID NO 20
<211> LENGTH: 48
<212> TYPE: DNA
<213> ORGANISM: Artificial
<220> FEATURE:
<223> OTHER INFORMATION: Synthetic NLS sequence

<400> SEQUENCE: 20
ctacatgttt ctaggcttct tcttggcgtt tccaattgcg ccggcgtg              48

<210> SEQ ID NO 21
<211> LENGTH: 6
<212> TYPE: PRT
<213> ORGANISM: Artificial
<220> FEATURE:
<223> OTHER INFORMATION: Synthetic NLS sequence

<400> SEQUENCE: 21

Pro Lys Lys Asn Arg Lys
1               5
```

<210> SEQ ID NO 22
<211> LENGTH: 1185
<212> TYPE: DNA
<213> ORGANISM: Artificial
<220> FEATURE:
<223> OTHER INFORMATION: Synthetic fusion protein pIX-GFP_NLS
<220> FEATURE:
<221> NAME/KEY: CDS
<222> LOCATION: (1)..(1185)

<400> SEQUENCE: 22

| | | | | | | | | | | | | | | | | |
|---|---|---|---|---|---|---|---|---|---|---|---|---|---|---|---|---|
| atg | agc | acc | aac | tcg | ttt | gat | gga | agc | att | gtg | agc | tca | tat | ttg | aca | 48 |
| Met | Ser | Thr | Asn | Ser | Phe | Asp | Gly | Ser | Ile | Val | Ser | Ser | Tyr | Leu | Thr | |
| 1 | | | | 5 | | | | | 10 | | | | | 15 | | |
| acg | cgc | atg | ccc | cca | tgg | gcc | ggg | gtg | cgt | cag | aat | gtg | atg | ggc | tcc | 96 |
| Thr | Arg | Met | Pro | Pro | Trp | Ala | Gly | Val | Arg | Gln | Asn | Val | Met | Gly | Ser | |
| | | | 20 | | | | | 25 | | | | | 30 | | | |
| agc | att | gat | ggt | cgc | ccc | gtc | ctg | ccc | gca | aac | tct | act | acc | ttg | acc | 144 |
| Ser | Ile | Asp | Gly | Arg | Pro | Val | Leu | Pro | Ala | Asn | Ser | Thr | Thr | Leu | Thr | |
| | | | | 35 | | | | | 40 | | | | | 45 | | |
| tac | gag | acc | gtg | tct | gga | acg | ccg | ttg | gag | act | gca | gcc | tcc | gcc | gcc | 192 |
| Tyr | Glu | Thr | Val | Ser | Gly | Thr | Pro | Leu | Glu | Thr | Ala | Ala | Ser | Ala | Ala | |
| | 50 | | | | | 55 | | | | | 60 | | | | | |
| gct | tca | gcc | gct | gca | gcc | acc | gcc | cgc | ggg | att | gtg | act | gac | ttt | gct | 240 |
| Ala | Ser | Ala | Ala | Ala | Ala | Thr | Ala | Arg | Gly | Ile | Val | Thr | Asp | Phe | Ala | |
| 65 | | | | | 70 | | | | | 75 | | | | | 80 | |
| ttc | ctg | agc | ccg | ctt | gca | agc | agt | gca | gct | tcc | cgt | tca | tcc | gcc | cgc | 288 |
| Phe | Leu | Ser | Pro | Leu | Ala | Ser | Ser | Ala | Ala | Ser | Arg | Ser | Ser | Ala | Arg | |
| | | | | 85 | | | | | 90 | | | | | 95 | | |
| gat | gac | aag | ttg | acg | gct | ctt | ttg | gca | caa | ttg | gat | tct | ttg | acc | cgg | 336 |
| Asp | Asp | Lys | Leu | Thr | Ala | Leu | Leu | Ala | Gln | Leu | Asp | Ser | Leu | Thr | Arg | |
| | | | | 100 | | | | | 105 | | | | | 110 | | |
| gaa | ctt | aat | gtc | gtt | tct | cag | cag | ctg | ttg | gat | ctg | cgc | cag | cag | gtt | 384 |
| Glu | Leu | Asn | Val | Val | Ser | Gln | Gln | Leu | Leu | Asp | Leu | Arg | Gln | Gln | Val | |
| | | | 115 | | | | | 120 | | | | | 125 | | | |
| tct | gcc | ctg | aag | gct | tcc | tcc | cct | ccc | aat | gcg | gtt | tgg | gat | cca | ccg | 432 |
| Ser | Ala | Leu | Lys | Ala | Ser | Ser | Pro | Pro | Asn | Ala | Val | Trp | Asp | Pro | Pro | |
| | 130 | | | | | 135 | | | | | 140 | | | | | |
| gtc | gcc | acc | atg | gtg | agc | aag | ggc | gag | gag | ctg | ttc | acc | ggg | gtg | gtg | 480 |
| Val | Ala | Thr | Met | Val | Ser | Lys | Gly | Glu | Glu | Leu | Phe | Thr | Gly | Val | Val | |
| 145 | | | | | 150 | | | | | 155 | | | | | 160 | |
| ccc | atc | ctg | gtc | gag | ctg | gac | ggc | gac | gta | aac | ggc | cac | aag | ttc | agc | 528 |
| Pro | Ile | Leu | Val | Glu | Leu | Asp | Gly | Asp | Val | Asn | Gly | His | Lys | Phe | Ser | |
| | | | | 165 | | | | | 170 | | | | | 175 | | |
| gtg | tcc | ggc | gag | ggc | gag | ggc | gat | gcc | acc | tac | ggc | aag | ctg | acc | ctg | 576 |
| Val | Ser | Gly | Glu | Gly | Glu | Gly | Asp | Ala | Thr | Tyr | Gly | Lys | Leu | Thr | Leu | |
| | | | | 180 | | | | | 185 | | | | | 190 | | |
| aag | ttc | atc | tgc | acc | acc | ggc | aag | ctg | ccc | gtg | ccc | tgg | ccc | acc | ctc | 624 |
| Lys | Phe | Ile | Cys | Thr | Thr | Gly | Lys | Leu | Pro | Val | Pro | Trp | Pro | Thr | Leu | |
| | | | 195 | | | | | 200 | | | | | 205 | | | |
| gtg | acc | acc | ctg | acc | tac | ggc | gtg | cag | tgc | ttc | agc | cgc | tac | ccc | gac | 672 |
| Val | Thr | Thr | Leu | Thr | Tyr | Gly | Val | Gln | Cys | Phe | Ser | Arg | Tyr | Pro | Asp | |
| | | 210 | | | | | 215 | | | | | 220 | | | | |
| cac | atg | aag | cag | cac | gac | ttc | ttc | aag | tcc | gcc | atg | ccc | gaa | ggc | tac | 720 |
| His | Met | Lys | Gln | His | Asp | Phe | Phe | Lys | Ser | Ala | Met | Pro | Glu | Gly | Tyr | |
| 225 | | | | | 230 | | | | | 235 | | | | | 240 | |
| gtc | cag | gag | cgc | acc | atc | ttc | ttc | aag | gac | gac | ggc | aac | tac | aag | acc | 768 |
| Val | Gln | Glu | Arg | Thr | Ile | Phe | Phe | Lys | Asp | Asp | Gly | Asn | Tyr | Lys | Thr | |
| | | | | 245 | | | | | 250 | | | | | 255 | | |
| cgc | gcc | gag | gtg | aag | ttc | gag | ggc | gac | acc | ctg | gtg | aac | cgc | atc | gag | 816 |

```
                                          Arg Ala Glu Val Lys Phe Glu Gly Asp Thr Leu Val Asn Arg Ile Glu
                                                          260                 265                 270 ctg aag ggc atc gac ttc aag gag gac ggc aac atc ctg ggg cac aag                  864
Leu Lys Gly Ile Asp Phe Lys Glu Asp Gly Asn Ile Leu Gly His Lys
            275                 280                 285 ctg gag tac aac tac aac agc cac aac gtc tat atc atg gcc gac aag                  912
Leu Glu Tyr Asn Tyr Asn Ser His Asn Val Tyr Ile Met Ala Asp Lys
        290                 295                 300 cag aag aac ggc atc aag gtg aac ttc aag atc cgc cac aac atc gag                  960
Gln Lys Asn Gly Ile Lys Val Asn Phe Lys Ile Arg His Asn Ile Glu
305                 310                 315                 320 gac ggc agc gtg cag ctc gcc gac cac tac cag cag aac acc ccc atc                 1008
Asp Gly Ser Val Gln Leu Ala Asp His Tyr Gln Gln Asn Thr Pro Ile
                325                 330                 335 ggc gac ggc ccc gtg ctg ctg ccc gac aac cac tac ctg agc acc cag                 1056
Gly Asp Gly Pro Val Leu Leu Pro Asp Asn His Tyr Leu Ser Thr Gln
            340                 345                 350 tcc gcc ctg agc aaa gac ccc aac gag aag cgc gat cac atg gtc ctg                 1104
Ser Ala Leu Ser Lys Asp Pro Asn Glu Lys Arg Asp His Met Val Leu
        355                 360                 365 ctg gag ttc gtg acc gcc gcc ggg atc act ctc ggc atg gac gag ctg                 1152
Leu Glu Phe Val Thr Ala Ala Gly Ile Thr Leu Gly Met Asp Glu Leu
370                 375                 380 tac aaa gat ccg aag aag aac cgc aaa ggt taa                                     1185
Tyr Lys Asp Pro Lys Lys Asn Arg Lys Gly
385                 390

<210> SEQ ID NO 23
<211> LENGTH: 394
<212> TYPE: PRT
<213> ORGANISM: Artificial
<220> FEATURE:
<223> OTHER INFORMATION: Synthetic Construct

<400> SEQUENCE: 23

Met Ser Thr Asn Ser Phe Asp Gly Ser Ile Val Ser Ser Tyr Leu Thr
1               5                   10                  15

Thr Arg Met Pro Pro Trp Ala Gly Val Arg Gln Asn Val Met Gly Ser
            20                  25                  30

Ser Ile Asp Gly Arg Pro Val Leu Pro Ala Asn Ser Thr Thr Leu Thr
        35                  40                  45

Tyr Glu Thr Val Ser Gly Thr Pro Leu Glu Thr Ala Ser Ala Ala
    50                  55                  60

Ala Ser Ala Ala Ala Thr Ala Arg Gly Ile Val Thr Asp Phe Ala
65                  70                  75                  80

Phe Leu Ser Pro Leu Ala Ser Ala Ala Ser Arg Ser Ser Ala Arg
                85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Asn Ala Val Trp Asp Pro Pro
130                 135                 140

Val Ala Thr Met Val Ser Lys Gly Glu Glu Leu Phe Thr Gly Val Val
145                 150                 155                 160

Pro Ile Leu Val Glu Leu Asp Gly Asp Val Asn Gly His Lys Phe Ser
                165                 170                 175

Val Ser Gly Glu Gly Glu Gly Asp Ala Thr Tyr Gly Lys Leu Thr Leu
```

```
              180              185              190
Lys Phe Ile Cys Thr Thr Gly Lys Leu Pro Val Pro Trp Pro Thr Leu
        195                 200                 205

Val Thr Thr Leu Thr Tyr Gly Val Gln Cys Phe Ser Arg Tyr Pro Asp
        210                 215                 220

His Met Lys Gln His Asp Phe Phe Lys Ser Ala Met Pro Glu Gly Tyr
225                 230                 235                 240

Val Gln Glu Arg Thr Ile Phe Phe Lys Asp Asp Gly Asn Tyr Lys Thr
                    245                 250                 255

Arg Ala Glu Val Lys Phe Glu Gly Asp Thr Leu Val Asn Arg Ile Glu
                260                 265                 270

Leu Lys Gly Ile Asp Phe Lys Glu Asp Gly Asn Ile Leu Gly His Lys
            275                 280                 285

Leu Glu Tyr Asn Tyr Asn Ser His Asn Val Tyr Ile Met Ala Asp Lys
        290                 295                 300

Gln Lys Asn Gly Ile Lys Val Asn Phe Lys Ile Arg His Asn Ile Glu
305                 310                 315                 320

Asp Gly Ser Val Gln Leu Ala Asp His Tyr Gln Gln Asn Thr Pro Ile
                325                 330                 335

Gly Asp Gly Pro Val Leu Leu Pro Asp Asn His Tyr Leu Ser Thr Gln
                340                 345                 350

Ser Ala Leu Ser Lys Asp Pro Asn Glu Lys Arg Asp His Met Val Leu
            355                 360                 365

Leu Glu Phe Val Thr Ala Ala Gly Ile Thr Leu Gly Met Asp Glu Leu
        370                 375                 380

Tyr Lys Asp Pro Lys Lys Asn Arg Lys Gly
385                 390

<210> SEQ ID NO 24
<211> LENGTH: 25
<212> TYPE: DNA
<213> ORGANISM: Artificial
<220> FEATURE:
<223> OTHER INFORMATION: Synthetic primer

<400> SEQUENCE: 24
ggatccttcc tcctcgggcg ggtgt                                        25

<210> SEQ ID NO 25
<211> LENGTH: 29
<212> TYPE: DNA
<213> ORGANISM: Artificial
<220> FEATURE:
<223> OTHER INFORMATION: Synthetic primer

<400> SEQUENCE: 25
aaccagcgct accatgagca ccaactcgt                                    29
```